US011119096B2

(12) United States Patent
Warthoe et al.

(10) Patent No.: US 11,119,096 B2
(45) Date of Patent: Sep. 14, 2021

(54) UNIVERSAL ASSAY FOR DETERMINING THE QUANTITY OF THERAPEUTIC MONOCLONAL ANTIBODIES AND THEIR CORRESPONDING ANTI-DRUG-ANTIBODIES IN SAMPLES

(71) Applicant: W. Health L.P., Nassau (BS)

(72) Inventors: Peter Warthoe, Copenhagen Ø (DK); Henrik Rindel Gudbergsen, Vanløse (DK)

(73) Assignee: W. Health L.P., Nassau (BS)

( * ) Notice: Subject to any disclaimer, the term of this patent is extended or adjusted under 35 U.S.C. 154(b) by 0 days.

(21) Appl. No.: 16/315,803

(22) PCT Filed: Jul. 3, 2017

(86) PCT No.: PCT/EP2017/066515
§ 371 (c)(1),
(2) Date: Jan. 7, 2019

(87) PCT Pub. No.: WO2018/007327
PCT Pub. Date: Jan. 11, 2018

(65) Prior Publication Data
US 2019/0162718 A1    May 30, 2019

(30) Foreign Application Priority Data
Jul. 8, 2016 (DK) .............. PA 201670515

(51) Int. Cl.
*G01N 33/542* (2006.01)
*G01N 33/53* (2006.01)
*G01N 33/68* (2006.01)

(52) U.S. Cl.
CPC ....... *G01N 33/542* (2013.01); *G01N 33/5306* (2013.01); *G01N 33/6854* (2013.01)

(58) Field of Classification Search
None
See application file for complete search history.

(56) References Cited

U.S. PATENT DOCUMENTS

| 2005/0009050 | A1* | 1/2005  | Nadeau  | C12Q 1/6804 |
|              |     |         |         | 435/6.18    |
| 2006/0034845 | A1  | 2/2006  | Silence et al. | |
| 2006/0275850 | A1* | 12/2006 | Groome  | C07K 16/26 |
|              |     |         |         | 435/7.92    |
| 2006/0287317 | A1* | 12/2006 | Smith   | C07C 233/60 |
|              |     |         |         | 514/237.5   |
| 2008/0008992 | A1* | 1/2008  | Ohshiro | G01N 33/5306 |
|              |     |         |         | 435/5       |
| 2011/0097723 | A1* | 4/2011  | Liu     | C12Q 1/6816 |
|              |     |         |         | 435/6.1     |
| 2012/0329172 | A1  | 12/2012 | Singh et al. | |
| 2013/0203075 | A1  | 8/2013  | Svenson et al. | |
| 2013/0295685 | A1  | 11/2013 | Singh et al. | |
| 2014/0045276 | A1  | 2/2014  | Singh et al. | |

FOREIGN PATENT DOCUMENTS

| EP | 2281631 A1 | 2/2011 | |
| JP | 2005077301 A | 3/2005 | |
| WO | 0218950 A1 | 3/2002 | |
| WO | 2008006588 A1 | 1/2008 | |
| WO | 2011056590 A1 | 5/2011 | |
| WO | 2014083520 A2 | 6/2014 | |
| WO | WO-2015128548 A1 * | 9/2015 | ......... G01N 33/6857 |
| WO | 2016097400 A1 | 6/2016 | |
| WO | 2016110595 A1 | 7/2016 | |

OTHER PUBLICATIONS

Leister et al. (Current Chemical Genomics 2011 vol. 5, p. 21-29) (Year: 2011).*
Lumigen (2013 Lab Protocol). (Year: 2013).*
Svenson et al. (Rheumatology 2007 vol. 46, p. 1828-1834) (Year: 2007).*
TechNote 2013 (Year: 2013).*
Langley et al. (International J. Dermatology 2010 vol. 49, p. 818-828) (Year: 2010).*
Bourdage et al. J. Pharmaceutical and Biomedical Analysis 2005 vol. 39, p. 685-690. (Year: 2005).*
Liu (II) Analytical Chemistry 2008 vol. 80, p. 7735-7741. (Year: 2008).*
Mould et al. British J. Clinical Pharmacology 2007 vol. 64, p. 278-291. (Year: 2007).*
Saraheimo et al. PLOSone 2013 vol. 8, p. e62739. (Year: 2013).*
Araujo et al. J. Pharmaceutical and Biomedical Anal. 2011 55:1041-1049 (Year: 2011).*
International Search Report, Application No. PCT/EP2017/066515, dated Aug. 2, 2017, 5 pages.
International Preliminary Report on Patentability and Written Opinion issued for International Application No. PCT/EP2017/066515, dated Jan. 8, 2019, 13 page.
Kelley, Marian, et al., "Theoretical Considerations and Practical Approaches to Address the Effect of Anti-drug Antibody (ADA) on Quantification of Biotherapeutics in Circulation", The AAPS Journal, vol. 15, Issue No. 3, Jul. 2013, pp. 646-658.
Koskinen, Janne O., et al. "A novel separation-free assay technique for serum antibodies using antibody bridging assay principle and two-photon excitation fluorometry", Journal of Immunological Methods, vol. 309, Issue No. 1-2, Feb. 20, 2006, pp. 11-24.

(Continued)

*Primary Examiner* — Changhwa J Cheu
(74) *Attorney, Agent, or Firm* — Ziegler IP Law Group, LLC

(57) ABSTRACT

A kit of parts and methods for determining the presence and quantity of one or more therapeutic monoclonal antibody drugs and/or therapeutic monoclonal antibody inhibitor drug antibodies in a biological sample, the method including providing a reaction liquid comprising the sample, a first conjugate with the target of the therapeutic monoclonal antibody and a first conjugated moiety and a second conjugate with the target of the therapeutic monoclonal antibody and a second conjugated moiety, followed by detecting the change in spectrophotometric signal when the complex between the therapeutic monoclonal antibody drug, the first conjugate and a the second conjugate forms.

19 Claims, No Drawings

(56) References Cited

OTHER PUBLICATIONS

Lee, Jean W., "ADME of monoclonal antibody biotherapeutics: knowledge gaps and emerging tools", "Bioanalysis", vol. 5, Issue No. 16, Aug. 1, 2013, pp. 2003-2014.

Aarden, Lucien, Sigrid R. Ruuls, and Gertjan Wolbink. "Immunogenicity of anti-tumor necrosis factor antibodies-toward improved methods of anti-antibody measurement." Current opinion in immunology 20.4 (2008): 431-435, 5 pages.

Bendtzen Klaus et al: "Individualized monitoring of drug bioavailability and immunogenicity in rheumatoid arthritis patients treated with the tumor necrosis factor alpha inhibitor infliximab", Arthritis & Rheumatism, vol. 54, No. 12, Dec. 2006 (Dec. 1, 2006), pp. 3782-3789, XP002626408, ISSN: 0004-3591, 8 pages.

Bendtzen, Klaus, and Morten Svenson. "Enzyme Immunoassays and Radioimmunoassays for Quantification of Anti-TNF Biopharmaceuticals and Anti-Drug Antibodies." Detection and Quantification of Antibodies to Biopharmaceuticals: Practical and Applied Considerations (2011): 81-101, 20 pages.

Bendtzen, Klaus. "Anti-TNF—biotherapies: perspectives for evidence-based personalized medicine." (2012), 13 pages.

Casper Steenholdt and Klaus Bendtzen. "Antibodies Against "Human" Biopharmaceuticals: Individualized Therapy with TNF-alpha Inhibitors Guided by Immunopharmacologic Assessments." Autoantibodies—(Third Edition)—(2014), Chapter 93, pp. 803-816, Elsevier B.V. ISBN: 978-0-444-56378—14 pages.

Eglen et al. (Current Chemical Genomics 2008 vol. 1, p. 2-10) (Year: 2008), 9 pages.

"List of Therapeutic monoclonal antibodies" Wikipedia article, Jul. 5, 2016, 21 pages.

Hock et al. "Development of an ELISA-Based Competitive Binding Assay for the Analysis of Drug Concentration and Antidrug Antibody Levels in Patients Receiving Adalimumab or lnfliximab" Copyright 2015 Wolters Kluwer Health, Inc. Ther Drug Monit, vol. 38, No. 1 Feb. 2016, 10 pages.

Japan Patent Office, Notice of Reasons for Refusal, Application No. 2019-500386, dated Mar. 23, 2021, 3 pages.

Japan Patent Office, Search Report by Registered Search Organization, Application No. JP2019500386, dated Mar. 15, 2021, 12 pages.

* cited by examiner

UNIVERSAL ASSAY FOR DETERMINING THE QUANTITY OF THERAPEUTIC MONOCLONAL ANTIBODIES AND THEIR CORRESPONDING ANTI-DRUG-ANTIBODIES IN SAMPLES

FIELD

The aspects of the disclosed embodiments relate to the monitoring or assaying of biological samples for the presence or absence of therapeutic monoclonal antibodies and their antibodies, such as anti-drug antibodies (ADA), in patients who may have developed an immune response to treatments with the therapeutic monoclonal antibody.

Accordingly, in one embodiment, the present disclosure relates to a method for determining the quantity of a therapeutic monoclonal antibody in a biological sample, preferably a blood sample, preferably a blood sample, preferably comprising less than 200 µl.

In a further embodiment, the present disclosure relates to a method for determining the quantity of one or more anti-drug antibodies (ADAs) against a therapeutic monoclonal antibody in a biological sample, preferably a blood sample, preferably comprising less than 200 µl.

In a further embodiment, the present disclosure relates to a method for determining the quantity of therapeutic monoclonal antibodies and their antibodies in a biological sample, preferably a blood sample, preferably a sample comprising less than 200 µl.

Further, the aspects of the disclosed embodiments relate to a kit of parts for determining the quantity of therapeutic monoclonal antibodies and their antibodies in a biological sample preferably a blood sample, preferably a sample comprising less than 200 µl.

BACKGROUND

Therapeutic monoclonal antibodies are increasingly used to combat a range of diseases.

However, patients being treated with therapeutic monoclonal antibodies may—for several reasons—respond poorly to their treatment, irrespective of previously being adequately responding to the therapy. Typically, the poor responders have a low amount of free drug (therapeutic monoclonal antibody) in their blood—lower than would be expected from the dose given. Accordingly, it is important to be able to monitor the level of drug (therapeutical monoclonal antibody) in the blood stream of a patient. If the level of drug in the blood is to low, an increase of the dose of the relevant therapeutic monoclonal antibody may be recommended. However, often, the reason for the poor response to treatment is that the immune system of the patient has developed antibodies against the particular therapeutic monoclonal antibody that the patient is being treated with. Accordingly, there is also a need in the art to monitor the (potential) presence of anti-drug antibodies (ADAs), i.e. antibodies against the therapeutic monoclonal antibody in the blood of the patient.

As one example, anti-tumor necrosis factor (TNF) therapy has become important for use in the management of several chronic immunoinflammatory diseases. Three recombinant anti-TNF alpha drugs are currently approved for clinical use in patients with various chronic inflammatory diseases such as rheumatoid arthritis (RA), Crohn's diseases and severe psoriasis: 1) Remicade™ (infliximab), a mouse-human IgG1-kappa anti-TNF-alpha monoclonal antibody, 2) Enbrel™ (etanercept), a fusion protein of human TNF receptor 2 and human IgG1, and 3) Humira™ (adalimumab), a fully human IgG1-kappa anti-TNF-alpha monoclonal antibody. Two other anti-TNF-alpha antibody constructs have shown promise in pivotal phase III trials in patients with some of the same diseases: 4) Cimzia™ CDP870 (certolizumab pegol), a PEGylated Fab fragment of a humanized anti-TNF-alpha monoclonal antibody, and 5) CNTO 148 (golimumab), a fully human IgG1-kappa anti-TNF-alpha monoclonal antibody. All of these proteins dramatically lower disease activity and, in some patients, may induce remission.

Unfortunately, however, not all patients respond favorably to anti-TNF alpha drugs. Some patients either do not respond at all (primary response failure) or they respond initially but have later relapses (secondary response failure) despite increased dosage and/or more frequent administration of the drugs. The reason(s) for these response failures are not always clear but interindividual and even intraindividual differences in bioavailability and pharmacokinetics may contribute to the problem. Immunogenicity of the drugs causing patients to develop anti-antibodies is a problem now recognized by many investigators, drug-controlling agencies, health insurance companies and drug manufacturers. Monitoring of patients for circulating levels of functional anti-TNF alpha drugs and anti-antibody development is therefore warranted so that administration can be tailored to the individual patient and so that prolonged therapies can be provided effectively and economically with little or no risk to the patients.

Following repeated infusions, the formation of neutralizing anti-TNF alpha drugs becomes a problem requiring increased doses or more frequent drug administration and may necessitate discontinuation of therapy because of secondary response failure and/or infusion-related side effects; this has been observed in both RA patients and in patients with other immunoinflammatory diseases. In clinical practice, however, patients with RA or any other chronic inflammatory disease treated with infliximab may differ considerably from the average patient in randomized clinical trials. For example, even though the initial bioavailability of infliximab approaches 100% because of the intravenous administration of the drug, differences in pharmacokinetics may result in individual patients having inadequate drug levels for extended periods of time between infusions. This problem can be exaggerated by the appearance of antibodies. A number of studies have reported a concentration-effect relationship of therapeutic proteins directed against TNF-alpha in patients with RA and Crohn's disease and an inverse relation between drug levels and ADA.

Similar problems occur during treatment with other therapeutic monoclonal antibodies.

Indeed, response failure due to induction of antibodies (ADAs) against biopharmaceuticals (in particular therapeutic monoclonal antibodies) is increasingly being realized. Development of host (patient) antibodies against biopharmaceuticals is particularly relevant when the drug is delivered chronically, i.e. periodic administration over a period of months or years. Anti-TNF alpha drugs are typically delivered chronically. When measuring ADAs, it is of importance is to identify the neutralizing ADAs from the non-neutralizing ADAs.

The development of host antibodies can be remedied by increasing dosage although this is typically a delayed and rather temporary response as the prescription dosage is typically only increased once patient symptoms noticeably deteriorate, and the increased dosage may well result in further augmentation of the patients' immune system. Typically, the more preferred remedy is to switch treatment regime and to use another drug (i.e. another therapeutic monoclonal antibody).

Accordingly, correctly assessing the quantity of therapeutic monoclonal antibodies and their antibodies (ADAs) in biological samples from patients poses ubiquitous challenges to medicinal practioners.

Different methods have been used to assess circulating levels of therapeutic monoclonal antibodies and their anti-drug-antibodies. Some of these are based on enzyme immunoassays (EIA) where the therapeutic monoclonal antibodies are immobilized on plastic beads or wells and bridging the binding of labeled therapeutic monoclonal antibodies by anti-drug-antibodies is used as readout. Other assays detect complexes of anti-drug-antibodies and therapeutic monoclonal antibodies by selective absorption for example by the binding of Fab of an immunoglobuline TNF alpha inhibitor to protein A, or to antibodies to anti-light chain Fab.

These methods, however, are cumbersome and specific towards a given therapeutic monoclonal antibodies (the method cannot be universally applied with function towards several different therapeutic monoclonal antibodies). Further, these methods may not be suitable for the detection and quantification of both therapeutic monoclonal antibodies and their antibodies in the same assay procedure.

US 2013/0295685 A1 and WO 2011/056590 A1 disclose mobility shift assays wherein a sample is contacted with a labeled TNF-alpha complex whereafter size exclusion chromatography is used to detect the presence of TNF-alpha inhibitory drug in the sample.

Hock et al. (The Drug Monit, Volume 38, Number 1, pages 32-41, February 2016) describe an enzyme-linked immunosorbent assay (ELISA)-based method for detection of both drug and ADA in patients receiving either adalimumab or infliximab.

These technique are, however, cumbersome and time-consuming.

Thus, the development of assays that can be used to monitor bioavailability of several therapeutic monoclonal antibodies and antibody development against several Therapeutic monoclonal antibodies is of direct clinical importance. In particular, there is a need in the art for fast and reliable methods which may be performed while patients are visiting the clinic.

Accordingly, there is a constant need in the art for alternative methods for determining therapeutic monoclonal antibodies and their antibodies, especially methods that are universally applicable and provide increased accuracy and give increased reproducibility.

to the aspects of the disclosed embodiments provide such methods and kits of parts for use in the methods.

In particular, there is a need in the art for kits of parts and methods which can be applied universally, in the sense that the medical practioner can assess different individual patients (patients potentially using different prescription medicaments) using the same assay. The aspects of the disclosed embodiments provide such methods and kits of parts.

Measurements of analytes in blood samples by patient- and user-friendly equipment conventionally aim at analysing blood samples consisting of less than 200 µl blood. Such quantities are easily obtained by the individual patients without being associated with serious health risks.

Thus, there is a need in the art for methods and devices capable of analysing therapeutic monoclonal antibodies and their antibodies quantities in blood samples. Such blood samples typically comprise less than 200 µl blood. Thus, more specifically, there is a need in the art for methods and devices capable of analysing therapeutic monoclonal antibodies and their antibodies quantities in blood samples comprising less than 200 µl blood, such as less than 180 µl blood, such as less than 150 µl, such as less than 100 µl, such as less than 50 µl, such as less than 20 µl, such as less than 10 µl, such as less than 9 µl, such as less than 8 µl, such as less than 7 µl, such as less than 6 µl, such as less than 5 µl, such as less than 4 µl, such as less than 3 µl, such as 2 µl or less blood. It is an object of the invention to provide such methods.

Another challenge is to increase the ease of each analysis, preferably to a level at which measurements of therapeutic monoclonal antibodies and their antibodies in blood can be made by the patient without the assistance of medicinal practioners. Further, it is also a challenge to bring down the costs to a level at which each measurement is affordable by the consumer.

Accordingly, there is a need in the art for methods and patient-friendly kits of parts allowing for accurately and easily measuring the level of therapeutic monoclonal antibodies and their antibodies in blood samples. Further, there is a need in the art for methods and kits of parts that allow for a simple and easy handling of samples and blood analysis. The aspects of the disclosed embodiments provide such methods.

Description

The aspects of the disclosed embodiments related to the detection and quantification of therapeutic monoclonal antibodies (drugs) in samples and in particular to the simultaneous detection of the therapeutic monoclonal antibody as well as the detection of antibodies against the therapeutic monoclonal antibody (anti-drug-antibodies) in samples.

Therapeutic Monoclonal Antibodies

A therapeutic monoclonal antibody according to the aspects of the disclosed embodiments is an antibody drug which excerts its function by binding a particular target in a human.

According to the aspects of the disclosed embodiments, "target" means a substance or structure comprising the molecular epitope to which the relevant therapeutic monoclonal antibody binds when excerting its relevant biological function.

Table 1 (ref Wikipedia "List of therapeutic monoclonal antibodies" 30 Jun. 2016; https://en.wikipedia.org/wiki/List_of_therapeutic_monoclonal_antibodies) includes approved and investigational therapeutic monoclonal antibodies ("drugs") as well as therapeutic monoclonal antibodies ("drugs") that have been withdrawn from the market. Consequently, the column "Use" does not necessarily indicate clinical usage. The drugs and targets appearing form Table 1 are particularly preferred therapeutic monoclonal antibodies and particularly preferred therapeutic monoclonal antibody targets according to the aspects of the disclosed embodiments.

The inventors have previously filed a patent application which relates to the inventive concept of the present application. However, that application was only directed to the detection of TNF-α binding drugs.

Since the filing of that application, the inventors have surprisingly found that the inventive concept is applicable to the detection of substantially all therapeutic monoclonal antibodies (drugs) in samples and in particular to the simultaneous detection of their corresponding antibodies (anti-drug-antibodies) in samples.

Accordingly, in one aspect, the aspects of the disclosed embodiments relate to methods for the detection of a therapeutic monoclonal antibody and/or its corresponding antidrug-antibody with the proviso that the therapeutic monoclonal antibody is not a TNF-α inhibitory drug or substance.

Accordingly, another aspect the of the disclosed embodiments relates to methods for the detection of a therapeutic monoclonal antibody and/or its corresponding anti-drug-antibody with the proviso that the universal ligand (target) used in the method is not TNF-α.

In one aspect, the disclosed embodiments relate to the detection of a therapeutic monoclonal antibody selected from the group comprising the therapeutic monoclonal antibodies; 3F8, 8H9, Abagovomab, Abciximab, Abituzumab, Abrilumab, Actoxumab, Abciximab, Abituzumab, Abrilumab, Actoxumab, Adalimumab, Adecatumumab, Aducanumab, Afutuzumab, Alacizumab pegol, ALD518, Alemtuzumab, Alirocumab, Altumomab pentetate, Amatuximab, Anatumomab mafenatox, Anetumab ravtansine, Anifrolumab, Anrukinzumab (=IMA-638) Apolizumab, Arcitumomab, Ascrinvacumab, Aselizumab, Atezolizumab, Atinumab, Atlizumab (=tocilizumab), Atorolimumab, Bapineuzumab, Basiliximab, Bavituximab, Bectumomab, Begelomab, Belimumab, Benralizumab, Bertilimumab, Besilesomab, Bevacizumab, Bezlotoxumab, Biciromab, Bimagrumab, Bimekizumab, Bivatuzumab mertansine, Blinatumomab, Blosozumab, Bococizumab, Brentuximab vedotin, Briakinumab, Brodalumab, Brolucizumab, Brontictuzumab, Canakinumab, Cantuzumab mertansine, Cantuzumab ravtansine, Caplacizumab, Capromab pendetide, Carlumab, Catumaxomab, cBR96-doxorubicin immunoconjugate, Cedelizumab, Cetuximab, Ch.14.18, Citatuzumab bogatox, Cixutumumab, Clazakizumab, Clenoliximab, Clivatuzumab tetraxetan, Codrituzumab, Coltuximab ravtansine, Conatumumab, Concizumab, Crenezumab, CR6261, Dacetuzumab, Daclizumab, Dalotuzumab, Dapirolizumab pegol, Daratumuma, Dectrekumab, Demcizumab, Denintuzumab mafodotin, Denosumab, Derlotuximab biotin, Detumomab, Dinutuximab, Diridavumab, Dorlimomab aritox, Drozitumab, Duligotumab, Dupilumab, Durvalumab, Dusigitumab, Ecromeximab, Eculizumab, Edobacomab, Edrecolomab, Efalizumab, Efungumab, Eldelumab, Elgemtumab, Elotuzumab, Elsilimomab, Emactuzumab, Emibetuzumab, Enavatuzumab, Enfortumab vedotin, Enlimomab pegol, Enoblituzumab, Enokizumab, Enoticumab, Ensituximab, Epitumomab cituxetan, Epratuzumab, Erlizumab, Ertumaxomab, Etaracizumab, Etrolizumab, Evinacumab, Evolocumab, Exbivirumab, Fanolesomab, Faralimomab, Farletuzumab, Fasinumab, FBTA05, Felvizumab, Fezakinumab, Ficlatuzumab, Figitumumab, Firivumab, Flanvotumab, Fletikumab, Fontolizumab, Foralumab, Foravirumab, Fresolimumab, Fulranumab, Futuximab, Galiximab, Ganitumab, Gantenerumab, Gavilimomab, Gemtuzumab ozogamicin, Gevokizumab, Girentuximab, Glembatumumab vedotin, Gomiliximab, Guselkumab, Ibalizumab, Ibritumomab tiuxetan, Icrucumab, Idarucizumab, Igovomab, IMAB362, Imalumab, Imciromab, Imgatuzumab, Inclacumab, Indatuximab ravtansine, Indusatumab vedotin, Intetumumab, Inolimomab, Inotuzumab ozogamicin, Ipilimumab, Iratumumab, Isatuximab, Itolizumab, Ixekizumab, Keliximab, Labetuzumab, Lambrolizumab, Lampalizumab, Lebrikizumab, Lemalesomab, Lenzilumab, Lerdelimumab, Lexatumumab, Libivirumab, Lifastuzumab vedotin, Ligelizumab, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, Mapatumumab, Margetuximab, Maslimomab, Mavrilimumab, Matuzumab, Mepolizumab, Metelimumab, Milatuzumab, Minretumomab, Mirvetuximab soravtansine, Mitumomab, Mogamulizumab, Morolimumab, Motavizumab, Moxetumomab pasudotox, Muromonab-CD3, Nacolomab tafenatox, Namilumab, Naptumomab estafenatox, Narnatumab[, Natalizumab, Nebacumab, Necitumumab, Nemolizumab, Nesvacumab, Nimotuzumab, Nivolumab, Nofetumomab merpentan, Obiltoxaximab, Obinutuzumab, Ocaratuzumab, Ocrelizumab, Odulimomab, Ofatumumab, Olaratumab, Olokizumab, Omalizumab, Onartuzumab, Ontuxizumab, Opicinumab, Oportuzumab monatox, Oregovomab, Orticumab, Otelixizumab, Otlertuzumab, Oxelumab, Ozanezumab, Pagibaximab, Palivizumab, Panitumumab, Pankomab, Panobacumab, Parsatuzumab, Pascolizumab, Pasotuxizumab, Pateclizumab, Patritumab, Pembrolizumab, Pemtumomab, Perakizumab, Pertuzumab, Pexelizumab, Pidilizumab, Pinatuzumab vedotin, Pintumomab, Placulumab, Polatuzumab vedotin, Ponezumab, Priliximab, Pritoxaximab, Pritumumab, PRO 140, Quilizumab, Tetulomab, Racotumomab, Radretumab, Rafivirumab, Ralpancizumab, Ramucirumab, Ranibizumab, Raxibacumab, Refanezumab, Regavirumab, Reslizumab, Rilotumumab, Rinucumab, Rituximab, Robatumumab, Roledumab, Romosozumab, Rontalizumab, Rovelizumab, Ruplizumab, Sacituzumab govitecan, Samalizumab, Sarilumab, Satumomab pendetide, Secukinumab, Seribantumab, Setoxaximab, Sevirumab, Sibrotuzumab, SGN-CD19A, SGN-CD33A, Sifalimumab, Siltuximab, Simtuzumab, Siplizumab, Sirukumab, Sofituzumab vedotin, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tarextumab, Tefibazumab, Telimomab aritox, Tenatumomab, Teneliximab, Teplizumab, Teprotumumab, Tesidolumab, TGN1412, Ticilimumab (=tremelimumab), Tildrakizumab, Tigatuzumab, TNX-650, Tocilizumab (=atlizumab, Toralizumab, Tosatoxumab, Tositumomab, Tovetumab, Tralokinumab, Trastuzumab, Trastuzumab emtansine, TRBS07, Tregalizumab, Tremelimumab, Trevogrumab, Tucotuzumab celmoleukin, Tuvirumab, Ublituximab, Ulocuplumab, Urelumab, Urtoxazumab, Ustekinumab, Vandortuzumab vedotin, Vantictumab, Vanucizumab, Vapaliximab, Varlilumab, Vatelizumab, Vedolizumab, Veltuzumab, Vepalimomab, Vesencumab, Visilizumab, Volociximab, Vorsetuzumab mafodotin, Votumumab, Zalutumumab, Zanolimumab, Zatuximab, Ziralimumab, Zolimomab aritox and the corresponding anti-drug antibody in a sample from a human patient.

In other words, the aspects of the disclosed embodiments relate to the detection of a therapeutic monoclonal antibody (and its corresponding anti-drug-antibody) selected from the group comprising therapeutic monoclonal antibodies targeting one of the molecular targets mentioned in Table 1, with the proviso that the group does not comprise therapeutic monoclonal antibodies targeting TNF-α.

TABLE 1

| Drug | Trade name | Type | Source | Target | Use |
|------|------------|------|--------|--------|-----|
| 3F8 |  | mab | mouse | GD2 | neuroblastoma |
| 8H9 |  | mab | mouse | B7-H3 | neuroblastoma, sarcoma, metastatic brain cancers |

TABLE 1-continued

| Drug | Trade name | Type | Source | Target | Use |
|---|---|---|---|---|---|
| Abagovomab | | mab | mouse | CA-125 (imitation) | ovarian cancer |
| Abciximab | ReoPro | Fab | chimeric | CD41 (integrin alpha-IIb) | platelet aggregation inhibitor |
| Abituzumab | | mab | humanized | CD51 | cancer |
| Abrilumab | | mab | human | integrin α4β7 | inflammatory bowel disease, ulcerative colitis, Crohn's disease |
| Actoxumab | | mab | human | *Clostridium difficile* | *Clostridium difficile* colitis |
| Adalimumab | Humira | mab | human | TNF-α | Rheumatoid arthritis, Crohn's Disease, Plaque Psoriasis, Psoriatic Arthritis, Ankylosing Spondylitis, Juvenile Idiopathic Arthritis, Hemolytic disease of the newborn |
| Adecatumumab | | mab | human | EpCAM | prostate and breast cancer |
| Aducanumab | | mab | human | beta-amyloid | Alzheimer's disease |
| Afelimomab | | F(ab')₂ | mouse | TNF-α | sepsis |
| Afutuzumab | | mab | humanized | CD20 | lymphoma |
| Alacizumab pegol | | F(ab')₂ | humanized | VEGFR2 | cancer |
| ALD518 | | ? | humanized | IL-6 | rheumatoid arthritis |
| Alemtuzumab | Lemtrada, Campath | mab | humanized | CD52 | Multiple sclerosis |
| Alirocumab | | mab | human | PCSK9 | hypercholesterolemia |
| Altumomab pentetate | Hybriceaker | mab | mouse | CEA | colorectal cancer (diagnosis) |
| Amatuximab | | mab | chimeric | mesothelin | cancer |
| Anatumomab mafenatox | | Fab | mouse | TAG-72 | non-small cell lung carcinoma |
| Anetumab ravtansine | | mab | human | MSLN | cancer |
| Anifrolumab | | mab | human | interferon α/β receptor | systemic lupus erythematosus |
| Anrukinzumab (=IMA-638) | | mab | humanized | IL-13 | ? |
| Apolizumab | | mab | humanized | HLA-DR ? | hematological cancers |
| Arcitumomab | CEA-Scan | Fab' | mouse | CEA | gastrointestinal cancers (diagnosis) |
| Ascrinvacumab | | mab | human | activin receptor-like kinase 1 | cancer |
| Aselizumab | | mab | humanized | L-selectin (CD62L) | severely injured patients |
| Atezolizumab | | mab | humanized | CD274 | cancer |
| Atinumab | | mab | human | RTN4 | ? |
| Atlizumab (=tocilizumab) | Actemra, RoActemra | mab | humanized | IL-6 receptor | rheumatoid arthritis |
| Atorolimumab | | mab | human | Rhesus factor | hemolytic disease of the newborn[citation needed] |
| Bapineuzumab | | mab | humanized | beta amyloid | Alzheimer's disease |
| Basiliximab | Simulect | mab | chimeric | CD25 (α chain of IL-2 receptor) | prevention of organ transplant rejections |
| Bavituximab | | mab | chimeric | phosphatidylserine | cancer, viral infections |
| Bectumomab | LymphoScan | Fab' | mouse | CD22 | non-Hodgkin's lymphoma (detection) |
| Begelomab | | mab | mouse | DPP4 | ? |
| Belimumab | Benlysta, LymphoStat-B | mab | human | BAFF | non-Hodgkin lymphoma etc. |
| Benralizumab | | mab | humanized | CD125 | asthma |
| Bertilimumab | | mab | human | CCL11 (eotaxin-1) | severe allergic disorders |

TABLE 1-continued

| Drug | Trade name | Type | Source | Target | Use |
|---|---|---|---|---|---|
| Besilesomab | Scintimun | mab | mouse | CEA-related antigen | inflammatory lesions and metastases (detection) |
| Bevacizumab | Avastin | mab | humanized | VEGF-A | metastatic cancer, retinopathy of prematurity |
| Bezlotoxumab | | mab | human | *Clostridium difficile* | *Clostridium difficile* colitis |
| Biciromab | FibriScint | Fab' | mouse | fibrin II, beta chain | thromboembolism (diagnosis) |
| Bimagrumab | | mab | human | ACVR2B | myostatin inhibitor |
| Bimekizumab | | mab | humanized | IL 17A and IL 17F | ? |
| Bivatuzumab mertansine | | mab | humanized | CD44 v6 | squamous cell carcinoma |
| Blinatumomab | | BiTE | mouse | CD19 | cancer |
| Blosozumab | | mab | humanized | SOST | osteoporosis |
| Bococizumab | | mab | humanized | neural apoptosis-regulated proteinase 1 | dyslipidemia |
| Brentuximab vedotin | | mab | chimeric | CD30 (TNFRSF8) | hematologic cancers |
| Briakinumab | | mab | human | IL-12, IL-23 | psoriasis, rheumatoid arthritis, inflammatory bowel diseases, multiple sclerosis |
| Brodalumab | | mab | human | IL-17 | inflammatory diseases |
| Brolucizumab | | mab | humanized | VEGFA | ? |
| Brontictuzumab | | mab | | Notch 1 | cancer |
| Canakinumab | Ilaris | mab | human | IL-1 ? | rheumatoid arthritis |
| Cantuzumab mertansine | | mab | humanized | mucin CanAg | colorectal cancer etc. |
| Cantuzumab ravtansine | | mab | humanized | MUC1 | cancers |
| Caplacizumab | | mab | humanized | VWF | thrombotic thrombocytopenic purpura, thrombosis |
| Capromab pendetide | Prostascint | mab | mouse | prostatic carcinoma cells | prostate cancer (detection) |
| Carlumab | | mab | human | MCP-1 | oncology/immune indications |
| Catumaxomab | Removab | 3funct | rat/mouse hybrid | EpCAM, CD3 | ovarian cancer, malignant ascites, gastric cancer |
| cBR96-doxorubicin immunoconjugate | | mab | humanized | Lewis-Y antigen | cancer |
| Cedelizumab | | mab | humanized | CD4 | prevention of organ transplant rejections, treatment of autoimmune diseases |
| Certolizumab pegol | Cimzia | Fab' | humanized | TNF-α | Crohn's disease |
| Cetuximab | Erbitux | mab | chimeric | EGFR | metastatic colorectal cancer and head and neck cancer |
| Ch.14.18 | | mab | chimeric | ??? | neuroblastoma |
| Citatuzumab bogatox | | Fab | humanized | EpCAM | ovarian cancer and other solid tumors |
| Cixutumumab | | mab | human | IGF-1 receptor | solid tumors |
| Clazakizumab | | mab | humanized | *Oryctolagus cuniculus* | rheumatoid arthritis |
| Clenoliximab | | mab | chimeric | CD4 | rheumatoid arthritis |
| Clivatuzumab tetraxetan | hPAM4-Cide | mab | humanized | MUC1 | pancreatic cancer |
| Codrituzumab | | mab | humanized | glypican 3 | cancer |
| Coltuximab ravtansine | | mab | chimeric | CD19 | cancer |
| Conatumumab | | mab | human | TRAIL-R2 | cancer |
| Concizumab | | mab | humanized | TFPI | bleeding |
| Crenezumab | | mab | humanized | 1-40-β-amyloid | Alzheimer's disease |

TABLE 1-continued

| Drug | Trade name | Type | Source | Target | Use |
|---|---|---|---|---|---|
| CR6261 | | mab | human | Influenza A hemagglutinin | infectious disease/influenza A |
| Dacetuzumab | | mab | humanized | CD40 | hematologic cancers |
| Daclizumab | Zenapax | mab | humanized | CD25 (α chain of IL-2 receptor) | prevention of organ transplant rejections |
| Dalotuzumab | | mab | humanized | insulin-like growth factor I receptor | cancer etc. |
| Dapirolizumab pegol | | mab | humanized | CD40 ligand | ? |
| Daratumuma | | mab | human | CD38 (cyclic ADP ribose hydrolase) | cancer |
| Dectrekumab | | mab | human | IL-13 | ? |
| Demcizumab | | mab | humanized | DLL4 | cancer |
| Denintuzumab mafodotin | | mab | humanized | CD19 | cancer |
| Denosumab | Prolia | mab | human | RANKL | osteoporosis, bone metastases etc. |
| Derlotuximab biotin | | mab | chimeric | histone complex | recurrent glioblastoma multiforme |
| Detumomab | | mab | mouse | B-lymphoma cell | lymphoma |
| Dinutuximab | | mab | chimeric | ganglioside GD2 | neuroblastoma |
| Diridavumab | | mab | human | hemagglutinin | influenza A |
| Dorlimomab aritox | | F(ab')$_2$ | mouse | ? | ? |
| Drozitumab | | mab | human | DR5 | cancer etc. |
| Duligotumab | | mab | human | HER3 | ? |
| Dupilumab | | mab | human | IL4 | atopic diseases |
| Durvalumab | | mab | human | CD274 | cancer |
| Dusigitumab | | mab | human | ILGF2 | cancer |
| Ecromeximab | | mab | chimeric | GD3 ganglioside | malignant melanoma |
| Eculizumab | Soliris | mab | humanized | C5 | paroxysmal nocturnal hemoglobinuria |
| Edobacomab | | mab | mouse | endotoxin | sepsis caused by Gram-negative bacteria |
| Edrecolomab | Panorex | mab | mouse | EpCAM | colorectal carcinoma |
| Efalizumab | Raptiva | mab | humanized | LFA-1 (CD11a) | psoriasis (blocks T-cell migration) |
| Efungumab | Mycograb | scFv | human | Hsp90 | invasive *Candida* infection |
| Eldelumab | | mab | human | interferon gamma-induced protein | Crohn's disease, ulcerative colitis |
| Elgemtumab | | mab | human | ERBB3 | cancer |
| Elotuzumab | | mab | humanized | SLAMF7 | multiple myeloma |
| Elsilimomab | | mab | mouse | IL-6 | ? |
| Emactuzumab | | mab | humanized | CSF1R | cancer |
| Emibetuzumab | | mab | humanized | HHGFR | cancer |
| Enavatuzumab | | mab | humanized | TWEAK receptor | cancer etc. |
| Enfortumab vedotin | | mab | human | AGS-22M6 | cancer expressing Nectin-4 |
| Enlimomab pegol | | mab | mouse | ICAM-1 (CD54) | ? |
| Enoblituzumab | | mab | humanized | B7-H3 | cancer |
| Enokizumab | | mab | humanized | IL9 | asthma |
| Enoticumab | | mab | human | DLL4 | ? |
| Ensituximab | | mab | chimeric | 5AC | cancer |
| Epitumomab cituxetan | | mab | mouse | episialin | ? |
| Epratuzumab | | mab | humanized | CD22 | cancer, SLE |
| Erlizumab | | F(ab')$_2$ | humanized | ITGB2 (CD18) | heart attack, stroke, traumatic shock |
| Ertumaxomab | Rexomun | 3funct | rat/mouse hybrid | HER2/neu, CD3 | breast cancer etc. |
| Etaracizumab | Abegrin | mab | humanized | integrin $\alpha_v\beta_3$ | melanoma, prostate cancer, ovarian cancer etc. |
| Etrolizumab | | mab | humanized | integrin $\alpha_7\beta_7$ | inflammatory bowel disease |
| Evinacumab | | mab | human | angiopoietin 3 | dyslipidemia |
| Evolocumab | | mab | human | PCSK9 | hypercholesterolemia |

TABLE 1-continued

| Drug | Trade name | Type | Source | Target | Use |
|---|---|---|---|---|---|
| Exbivirumab | | mab | human | hepatitis B surface antigen | hepatitis B |
| Fanolesomab | NeutroSpec | mab | mouse | CD15 | appendicitis (diagnosis) |
| Faralimomab | | mab | mouse | interferon receptor | ? |
| Farletuzumab | | mab | humanized | folate receptor 1 | ovarian cancer |
| Fasinumab | | mab | human | HNGF | acute sciatic pain |
| FBTA05 | Lymphomun | 3funct | rat/mouse hybrid | CD20 | chronic lymphocytic leukaemia |
| Felvizumab | | mab | humanized | respiratory syncytial virus | respiratory syncytial virus infection |
| Fezakinumab | | mab | human | IL-22 | rheumatoid arthritis, psoriasis |
| Ficlatuzumab | | mab | humanized | HGF | cancer etc. |
| Figitumumab | | mab | human | IGF-1 receptor | adrenocortical carcinoma, non-small cell lung carcinoma etc. |
| Firivumab | | mab | human | influenza A virus hemagglutinin | ? |
| Flanvotumab | | mab | human | TYRP1 (glycoprotein 75) | melanoma |
| Fletikumab | | mab | human | IL 20 | rheumatoid arthritis |
| Fontolizumab | HuZAF | mab | humanized | IFN-γ | Crohn's disease etc. |
| Foralumab | | mab | human | CD3 epsilon | ? |
| Foravirumab | | mab | human | rabies virus glycoprotein | rabies (prophylaxis) |
| Fresolimumab | | mab | human | TGF-β | idiopathic pulmonary fibrosis, focal segmental glomerulosclerosis, cancer |
| Fulranumab | | mab | human | NGF | pain |
| Futuximab | | mab | chimeric | EGFR | ? |
| Galiximab | | mab | chimeric | CD80 | B-cell lymphoma |
| Ganitumab | | mab | human | IGF-I | cancer |
| Gantenerumab | | mab | human | beta amyloid | Alzheimer's disease |
| Gavilimomab | | mab | mouse | CD147 (basigin) | graft versus host disease |
| Gemtuzumab ozogamicin | Mylotarg | mab | humanized | CD33 | acute myelogenous leukemia |
| Gevokizumab | | mab | humanized | IL-1β | diabetes etc. |
| Girentuximab | Rencarex | mab | chimeric | carbonic anhydrase 9 (CA-IX) | clear cell renal cell carcinoma[81] |
| Glembatumumab vedotin | | mab | human | GPNMB | melanoma, breast cancer |
| Golimumab | Simponi | mab | human | TNF-α | rheumatoid arthritis, psoriatic arthritis, ankylosing spondylitis |
| Gomiliximab | | mab | chimeric | CD23 (IgE receptor) | allergic asthma |
| Guselkumab | | mab | human | IL23 | psoriasis |
| Ibalizumab | | mab | humanized | CD4 | HIV infection |
| Ibritumomab tiuxetan | Zevalin | mab | mouse | CD20 | non-Hodgkin's lymphoma |
| Icrucumab | | mab | human | VEGFR-1 | cancer etc. |
| Idarucizumab | | mab | humanized | dabigatran | reversal of anticoagulant effects of dabigatran |
| Igovomab | Indimacis-125 | F(ab')$_2$ | mouse | CA-125 | ovarian cancer (diagnosis) |
| IMAB362 | | mab | human | CLDN18.2 | gastrointestinal adenocarcinomas and pancreatic tumor |
| Imalumab | | mab | human | MIF | cancer |
| Imciromab | Myoscint | mab | mouse | cardiac myosin | cardiac imaging |
| Imgatuzumab | | mab | humanized | EGFR | cancer |
| Inclacumab | | mab | human | selectin P | ? |
| Indatuximab ravtansine | | mab | chimeric | SDC1 | cancer |

TABLE 1-continued

| Drug | Trade name | Type | Source | Target | Use |
|---|---|---|---|---|---|
| Indusatumab vedotin | | mab | human | GUCY2C | cancer |
| Infliximab | Remicade | mab | chimeric | TNF-α | rheumatoid arthritis, ankylosing spondylitis, psoriatic arthritis, psoriasis, Crohn's disease, ulcerative colitis |
| Intetumumab | | mab | human | CD51 | solid tumors (prostate cancer, melanoma) |
| Inolimomab | | mab | mouse | CD25 (α chain of IL-2 receptor) | graft versus host disease |
| Inotuzumab ozogamicin | | mab | humanized | CD22 | cancer |
| Ipilimumab | Yervoy | mab | human | CD152 | melanoma |
| Iratumumab | | mab | human | CD30 (TNFRSF8) | Hodgkin's lymphoma |
| Isatuximab | | mab | chimeric | CD38 | cancer |
| Itolizumab | | mab | humanized | CD6 | ? |
| Ixekizumab | | mab | humanized | IL 17A | autoimmune diseases |
| Keliximab | | mab | chimeric | CD4 | chronic asthma |
| Labetuzumab | CEA-Cide | mab | humanized | CEA | colorectal cancer |
| Lambrolizumab | | mab | humanized | PDCD1 | antineoplastic agent |
| Lampalizumab | | mab | humanized | CFD | ? |
| Lebrikizumab | | mab | humanized | IL-13 | asthma |
| Lemalesomab | | mab | mouse | NCA-90 (granulocyte antigen) | diagnostic agent |
| Lenzilumab | | mab | human | CSF2 | ? |
| Lerdelimumab | | mab | human | TGF beta 2 | reduction of scarring after glaucoma surgery |
| Lexatumumab | | mab | human | TRAIL-R2 | cancer |
| Libivirumab | | mab | human | hepatitis B surface antigen | hepatitis B |
| Lifastuzumab vedotin | | mab | humanized | phosphate-sodium co-transporter | cancer |
| Ligelizumab | | mab | humanized | IGHE | severe asthma and chronic spontaneous urticaria |
| Lilotomab satetraxetan | | mab | mouse | CD37 | cancer |
| Lintuzumab | | mab | humanized | CD33 | cancer |
| Lirilumab | | mab | human | KIR2D | ? |
| Lodelcizumab | | mab | humanized | PCSK9 | hypercholesterolemia |
| Lokivetmab | | mab | veterinary | *Canis lupus familiaris* IL31 | ? |
| Lorvotuzumab mertansine | | mab | humanized | CD56 | cancer |
| Lucatumumab | | mab | human | CD40 | multiple myeloma, non-Hodgkin's lymphoma, Hodgkin's lymphoma |
| Lulizumab pegol | | mab | humanized | CD28 | autoimmune diseases |
| Lumiliximab | | mab | chimeric | CD23 (IgE receptor) | chronic lymphocytic leukemia |
| Lumretuzumab | | mab | humanized | ERBB3 | cancer |
| Mapatumumab | | mab | human | TRAIL -R1 | cancer |
| Margetuximab | | mab | humanized | ch4D5 | cancer |
| Maslimomab | | ? | mouse | T-cell receptor | ? |
| Mavrilimumab | | mab | human | GMCSF receptor α-chain | rheumatoid arthritis |
| Matuzumab | | mab | humanized | EGFR | colorectal, lung and stomach cancer |
| Mepolizumab | Bosatria | mab | humanized | IL-5 | asthma and white blood cell diseases |
| Metelimumab | | mab | human | TGF beta 1 | systemic scleroderma |

TABLE 1-continued

| Drug | Trade name | Type | Source | Target | Use |
|---|---|---|---|---|---|
| Milatuzumab | | mab | humanized | CD74 | multiple myeloma and other hematological malignancies |
| Minretumomab | | mab | mouse | TAG-72 | tumor detection (and therapy?) |
| Mirvetuximab soravtansine | | mab | chimeric | folate receptor alpha | cancer |
| Mitumomab | | mab | mouse | GD3 ganglioside | small cell lung carcinoma |
| Mogamulizumab | | mab | humanized | CCR4 | cancer |
| Morolimumab | | mab | human | Rhesus factor | ? |
| Motavizumab | Numax | mab | humanized | respiratory syncytial virus | respiratory syncytial virus (prevention) |
| Moxetumomab pasudotox | | mab | mouse | CD22 | cancer |
| Muromonab-CD3 | Orthoclone OKT3 | mab | mouse | CD3 | prevention of organ transplant rejections |
| Nacolomab tafenatox | | Fab | mouse | C242 antigen | colorectal cancer |
| Namilumab | | mab | human | CSF2 | ? |
| Naptumomab estafenatox | | Fab | mouse | 5T4 | non-small cell lung carcinoma, renal cell carcinoma |
| Narnatumab[ | | mab | human | RON | cancer |
| Natalizumab | Tysabri | mab | humanized | integrin $\alpha_4$ | multiple sclerosis, Crohn's disease |
| Nebacumab | | mab | human | endotoxin | sepsis |
| Necitumumab | | mab | human | EGFR | non-small cell lung carcinoma |
| Nemolizumab | | mab | humanized | IL31RA | ? |
| Nerelimomab | | mab | mouse | TNF-$\alpha$ | ? |
| Nesvacumab | | mab | human | angiopoietin 2 | cancer |
| Nimotuzumab | Theracim, Theraloc | mab | humanized | EGFR | squamous cell carcinoma, head and neck cancer, nasopharyngeal cancer, glioma |
| Nivolumab | Opdivo | mab | human | PD-1 | cancer |
| Nofetumomab merpentan | Verluma | Fab | mouse | ? | cancer (diagnosis) |
| Obiltoxaximab | | mab | chimeric | *Bacillusanthracis* anthrax | *Bacillus anthracis* spores |
| Obinutuzumab | Gazyva | mab | humanized | CD20 | Chronic lymphatic leukemia |
| Ocaratuzumab | | mab | humanized | CD20 | cancer |
| Ocrelizumab | | mab | humanized | CD20 | rheumatoid arthritis, lupus erythematosus etc. |
| Odulimomab | | mab | mouse | LFA-1 (CD11a) | prevention of organ transplant rejections, immunological diseases |
| Ofatumumab | Arzerra | mab | human | CD20 | chronic lymphocytic leukemia etc. |
| Olaratumab | | mab | human | PDGF-R $\alpha$ | cancer |
| Olokizumab | | mab | humanized | IL6 | ? |
| Omalizumab | Xolair | mab | humanized | IgE Fc region | allergic asthma |
| Onartuzumab | | mab | humanized | human scatter factor receptor kinase | cancer |
| Ontuxizumab | | mab | chimeric/humanized | TEM1 | cancer |
| Opicinumab | | mab | human | LINGO-1 | multiple sclerosis |
| Oportuzumab monatox | | scFv | humanized | EpCAM | cancer |
| Oregovomab | OvaRex | mab | mouse | CA-125 | ovarian cancer |
| Orticumab | | mab | human | oxLDL | ? |
| Otelixizumab | | mab | chimeric/humanized | CD3 | diabetes mellitus type 1 |
| Otlertuzumab | | mab | humanized | CD37 | cancer |
| Oxelumab | | mab | human | OX-40 | asthma |
| Ozanezumab | | mab | humanized | NOGO-A | ALS and multiple sclerosis |

TABLE 1-continued

| Drug | Trade name | Type | Source | Target | Use |
|---|---|---|---|---|---|
| Ozoralizumab | | mab | humanized | TNF-α | inflammation |
| Pagibaximab | | mab | chimeric | lipoteichoic acid | sepsis (*Staphylococcus*) |
| Palivizumab | Synagis, Abbosynagis | mab | humanized | F protein of respiratory syncytial virus | respiratory syncytial virus (prevention) |
| Panitumumab | Vectibix | mab | human | EGFR | colorectal cancer |
| Pankomab | | mab | humanized | tumor specific glycosylation of MUC1 | ovarian cancer |
| Panobacumab | | mab | human | *Pseudomonas aeruginosa* | *Pseudomonas aeruginosa* infection |
| Parsatuzumab | | mab | human | EGFL7 | cancer |
| Pascolizumab | | mab | humanized | IL-4 | asthma |
| Pasotuxizumab | | mab | chimeric/humanized | folate hydrolase | cancer |
| Pateclizumab | | mab | humanized | LTA | TNF |
| Patritumab | | mab | human | HER3 | cancer |
| Pembrolizumab | | mab | humanized | PDCD1 | cancer etc. |
| Pemtumomab | Theragyn | ? | mouse | MUC1 | cancer |
| Perakizumab | | mab | humanized | IL 17A | arthritis |
| Pertuzumab | Omnitarg | mab | humanized | HER2/neu | cancer |
| Pexelizumab | | scFv | humanized | C5 | reduction of side effects of cardiac surgery |
| Pidilizumab | | mab | humanized | PD-1 | cancer and infectious diseases |
| Pinatuzumab vedotin | | mab | humanized | CD22 | cancer |
| Pintumomab | | mab | mouse | adenocarcinoma antigen | adenocarcinoma (imaging) |
| Placulumab | | mab | human | human TNF | ? |
| Polatuzumab vedotin | | mab | humanized | CD79B | cancer |
| Ponezumab[120] | | mab | humanized | human beta-amyloid | Alzheimer's disease |
| Priliximab | | mab | chimeric | CD4 | Crohn's disease, multiple sclerosis |
| Pritoxaximab | | mab | chimeric | *E. coli* shiga toxin type-1 | ? |
| Pritumumab | | mab | human | vimentin | brain cancer |
| PRO 140 | | ? | humanized | CCR5 | HIV infection |
| Quilizumab | | mab | humanized | IGHE | asthma |
| Tetulomab | | mab | humanized | CD37 | cancer [121] |
| Racotumomab | | mab | mouse | N-glycolylneuraminic acid | cancer |
| Radretumab | | mab | human | fibronectin extra domain-B | cancer |
| Rafivirumab | | mab | human | rabies virus glycoprotein | rabies (prophylaxis) |
| Ralpancizumab[ | | mab | humanized | neural apoptosis-regulated proteinase 1 | dyslipidemia |
| Ramucirumab | Cyramza | mab | human | VEGFR2 | solid tumors |
| Ranibizumab | Lucentis | Fab | humanized | VEGF-A | macular degeneration (wet form) |
| Raxibacumab | | mab | human | anthrax toxin, protective antigen | anthrax (prophylaxis and treatment) |
| Refanezumab | | mab | humanized | myelin-associated glycoprotein | recovery of motor function after stroke |
| Regavirumab | | mab | human | cytomegalovirus glycoprotein B | cytomegalovirus infection |
| Reslizumab | | mab | humanized | IL-5 | inflammations of the airways, skin and gastrointestinal tract |
| Rilotumumab | | mab | human | HGF | solid tumors |
| Rinucumab | | mab | human | platelet-derived growth factor receptor beta | neovascular age-related macular degeneration |
| Rituximab | MabThera, Rituxan | mab | chimeric | CD20 | lymphomas, leukemias, some autoimmune disorders |

TABLE 1-continued

| Drug | Trade name | Type | Source | Target | Use |
|---|---|---|---|---|---|
| Robatumumab | | mab | human | IGF-1 receptor | cancer |
| Roledumab | | mab | human | RHD | ? |
| Romosozumab | | mab | humanized | sclerostin | osteoporosis |
| Rontalizumab | | mab | humanized | IFN-α | systemic lupus erythematosus |
| Rovelizumab | LeukArrest | mab | humanized | CD11, CD18 | haemorrhagic shock etc. |
| Ruplizumab | Antova | mab | humanized | CD154 (CD40L) | rheumatic diseases |
| Sacituzumab govitecan | | mab | humanized | tumor-associated calcium signal transducer 2 | cancer |
| Samalizumab | | mab | humanized | CD200 | cancer |
| Sarilumab | | mab | human | IL6 | rheumatoid arthritis, ankylosing spondylitis |
| Satumomab pendetide | | mab | mouse | TAG-72 | cancer (diagnosis) |
| Secukinumab | | mab | human | IL 17A | uveitis, rheumatoid arthritis psoriasis |
| Seribantumab | | mab | human | ERBB3 | cancer |
| Setoxaximab | | mab | chimeric | *E. coli* shiga toxin type-2 | ? |
| Sevirumab | | ? | human | cytomegalovirus | cytomegalovirus infection |
| Sibrotuzumab | | mab | humanized | FAP | cancer |
| SGN-CD19A | | mab | humanized | CD19 | acute lymphoblastic leukemia and B-cell non-Hodgkin lymphoma |
| SGN-CD33A | | mab | humanized | CD33 | Acute myeloid leukemia |
| Sifalimumab | | mab | humanized | IFN-α | SLE, dermatomyositis, polymyositis |
| Siltuximab | | mab | chimeric | IL-6 | cancer |
| Simtuzumab | | mab | humanized | LOXL2 | fibrosis |
| Siplizumab | | mab | humanized | CD2 | psoriasis, graft-versus-host disease (prevention) |
| Sirukumab | | mab | human | IL-6 | rheumatoid arthritis |
| Sofituzumab vedotin | | mab | humanized | CA 125 | ovarian cancer |
| Solanezumab | | mab | humanized | beta amyloid | Alzheimer's disease |
| Solitomab | | mab | mouse | EpCAM | ? |
| Sonepcizumab | | ? | humanized | sphingosine-1-phosphate | choroidal and retinal neovascularization |
| Sontuzumab | | mab | humanized | episialin | ? |
| Stamulumab | | mab | human | myostatin | muscular dystrophy |
| Sulesomab | LeukoScan | Fab' | mouse | NCA-90 (granulocyte antigen) | osteomyelitis (imaging) |
| Suvizumab | | mab | humanized | HIV-1 | viral infections |
| Tabalumab | | mab | human | BAFF | B-cell cancers |
| Tacatuzumab tetraxetan | AFP-Cide | mab | humanized | alpha-fetoprotein | cancer |
| Tadocizumab | | Fab | humanized | integrin $\alpha_{IIb}\beta_3$ | percutaneous coronary intervention |
| Talizumab | | mab | humanized | IgE | allergic reaction |
| Tanezumab | | mab | humanized | NGF | pain |
| Taplitumomab paptox | | mab | mouse | CD19 | cancer[citation needed] |
| Tarextumab | | mab | human | Notch receptor | cancer |
| Tefibazumab | Aurexis | mab | humanized | clumping factor A | *Staphylococcus aureus* infection |
| Telimomab aritox | | Fab | mouse | ? | ? |
| Tenatumomab | | mab | mouse | tenascin C | cancer |
| Teneliximab | | mab | chimeric | CD40 | ? |
| Teplizumab | | mab | humanized | CD3 | diabetes mellitus type 1 |
| Teprotumumab | | mab | human | CD221 | hematologic tumors |
| Tesidolumab | | mab | human | C5 | ? |
| TGN1412 | | ? | humanized | CD28 | chronic lymphocytic leukemia, rheumatoid arthritis |

TABLE 1-continued

| Drug | Trade name | Type | Source | Target | Use |
|---|---|---|---|---|---|
| Ticilimumab (=tremelimumab) | | mab | human | CTLA-4 | cancer |
| Tildrakizumab | | mab | humanized | IL23 | immunologically mediated inflammatory disorders |
| Tigatuzumab | | mab | humanized | TRAIL-R2 | cancer |
| TNX-650 | | ? | humanized | IL-13 | Hodgkin's lymphoma |
| Tocilizumab (=atlizumab) | Actemra, RoActemra | mab | humanized | IL-6 receptor | rheumatoid arthritis |
| Toralizumab | | mab | humanized | CD154 (CD40L) | rheumatoid arthritis, lupus nephritis etc. |
| Tosatoxumab | | mab | human | *Staphylococcus aureus* | ? |
| Tositumomab | Bexxar | ? | mouse | CD20 | follicular lymphoma |
| Tovetumab | | mab | human | CD140a | cancer |
| Tralokinumab | | mab | human | IL-13 | asthma etc. |
| Trastuzumab | Herceptin | mab | humanized | HER2/neu | breast cancer |
| Trastuzumab emtansine | Kadcyla | mab | humanized | HER2/neu | breast cancer |
| TRBS07 | Ektomab | 3funct | ? | GD2 | melanoma |
| Tregalizumab | | mab | humanized | CD4 | ? |
| Tremelimumab | | mab | human | CTLA-4 | cancer |
| Trevogrumab | | mab | human | growth differentiation factor 8 | muscle atrophy due to orthopedic disuse and sarcopenia |
| Tucotuzumab celmoleukin | | mab | humanized | EpCAM | cancer |
| Tuvirumab | | ? | human | hepatitis B virus | chronic hepatitis B |
| Ublituximab | | mab | chimeric | MS4A1 | cancer |
| Ulocuplumab | | mab | human | C-X-C chemokine receptor type 4 | hematologic malignancies |
| Urelumab | | mab | human | 4-1BB | cancer etc. |
| Urtoxazumab | | mab | humanized | *Escherichia coli* | diarrhoea caused by *E. coli* |
| Ustekinumab | Stelara | mab | human | IL-12, IL-23 | multiple sclerosis, psoriasis, psoriatic arthritis |
| Vandortuzumab vedotin | | mab | humanized | STEAP1 | cancer |
| Vantictumab | | mab | human | Frizzled receptor | cancer |
| Vanucizumab | | mab | humanized | angiopoietin 2 | cancer |
| Vapaliximab | | mab | chimeric | AOC3 (VAP-1) | ? |
| Varlilumab | | mab | human | CD27 | ? |
| Vatelizumab[ | | mab | humanized | ITGA2 | ? |
| Vedolizumab | | mab | humanized | integrin $\alpha_4\beta_7$ | Crohn's disease, ulcerative colitis |
| Veltuzumab | | mab | humanized | CD20 | non-Hodgkin's lymphoma |
| Vepalimomab | | mab | mouse | AOC3 (VAP-1) | inflammation |
| Vesencumab | | mab | human | NRP1 | ? |
| Visilizumab | Nuvion | mab | humanized | CD3 | Crohn's disease, ulcerative colitis |
| Volociximab | | mab | chimeric | integrin $\alpha_5\beta_1$ | solid tumors |
| Vorsetuzumab mafodotin | | mab | humanized | CD70 | cancer |
| Votumumab | HumaSPECT | mab | human | tumor antigen CTAA16.88 | colorectal tumors |
| Zalutumumab | HuMax-EGFr | mab | human | EGFR | squamous cell carcinoma of the head and neck |
| Zanolimumab | HuMax-CD4 | mab | human | CD4 | rheumatoid arthritis, psoriasis, T-cell lymphoma |
| Zatuximab | | mab | chimeric | HER1 | cancer |
| Ziralimumab | | mab | human | CD147 (basigin) | ? |
| Zolimomab aritox | | mab | mouse | CD5 | systemic lupus erythematosus, graft-versus-host disease |

A particularly preferred aspect of the disclosed embodiments relates to the detection of a therapeutical monoclonal antibody targeting IL17A, such as brodalumab, secukinumab and ixekizumab and the corresponding anti-drug-antibody.

As stated above, there is a ubiquitous need in the art for methods and patient-friendly kits of parts providing accurate, sensitive and reproducible measurements of the level of (multiple) therapeutic monoclonal antibodies and their antibodies in biological samples. In some embodiments, the biological sample according to the disclosed embodiments is selected from the group consisting of blood, blood serum, lymph fluid, lymph node tissue, spleen tissue, bone marrow, or an immunoglobulin enriched fraction derived from one or more of these tissues. According to the present invention, a blood sample means a sample of full blood from a patient or a material derived therefrom (such as serum).

The aspects of the disclosed embodiments provide a highly effective and sensitive assay for detection of the level of therapeutic monoclonal antibodies and their antibodies in samples.

The basic principle of the assay is the use of a "labeled" target of the therapeutic monoclonal antibody as the universal ligand specific to the therapeutic monoclonal antibody. The universal ligand is labeled in the sense that it forms a molecular complex in the presence of the therapeutic monoclonal antibody. The hereby formed complex was found capable of ameliorating a spectrophotometric signal. The reason for this ability is believed to be the bi-functionality of (most) monoclonal antibodies, carrying two epitope binding sequences. Thereby, a single therapeutic monoclonal antibody is capable of binding to and bringing together two (identical or different) moieties. Thus, a plurality of therapeutic monoclonal antibodies and a plurality of targets are brought together in a large molecular network which (when using solid particles) changes the absorbance of the sample in a spectrophotometric test. In alternative aspects, the moieties may be dual sets of functional moieties, such as an enzyme and its substrate or a fluorophore and a quencher.

Thus, in a first embodiment, the invention provides a method for determining the presence and quantity of a therapeutic monoclonal antibody in one or more blood samples, the method comprising the steps of:

a. providing a first conjugate comprising the target of the therapeutic monoclonal antibody and a first conjugated moiety,
b. providing a second conjugate comprising the target of the therapeutic monoclonal antibody and a second conjugated moiety,
c. providing a reaction liquid comprising the first and the second conjugates and contacting the sample with the reaction liquid, whereby a detection liquid comprising the sample potentially comprising the therapeutic monoclonal antibody and the first and the second conjugates is formed,
d. detecting the change in spectrophotometric signal following contacting the sample with the reaction liquid in step c, (when the complex comprising the therapeutic monoclonal antibody and the first and the second conjugates is formed), and
e. determining the quantity of the therapeutic monoclonal antibody Preferably, step e is performed by comparing the obtained results with an internal standard.

The internal standard may be provided by a preproduced standard curve which plots the signal produced by the above method performed on a corresponding sample having a known (spiked) content of the particular therapeutic monoclonal antibody drug. The assay performs differently for different therapeutic monoclonal antibody drugs due to differences in binding affinity necessitating different internal standards for different therapeutic monoclonal antibody drugs.

In one embodiment of the present disclosure, the level of haemoglobin is also measured and used to assess the relative level of therapeutic monoclonal antibodies and their antibodies in the blood sample.

The First and the Second Conjugates

The conjugates (the first and the second) according to the disclosed embodiments may in some embodiments be identical and in other embodiments function pairwise.

In a highly preferred embodiment, the conjugates are solid particles coated with the target of the relevant therapeutic monoclonal antibody. In these embodiments, the first and the second moieties are solid particles and the detectable signal provided by the formation of the complex comprising the relevant therapeutic monoclonal antibody and the first and the second conjugates may for example be a change in turbidity of the detection liquid. It was surprisingly observed that in such embodiments, a single therapeutic monoclonal antibody drug was capable of binding and immobilising more than one of the conjugates (particles), thereby producing a detectable mesh proportional to the concentration of drug.

However, it was found that the addition of a further ligand, a therapeutic monoclonal antibody-binding agent, binding individual therapeutic monoclonal antibody together at sites other than the binding site for the target of the relevant therapeutic monoclonal antibody increased the assay performance drastically. The therapeutic monoclonal antibody-binding agent must be able to bind two therapeutical monoclonal antibodies together at sites other than the binding site for the target for the relevant therapeutical monoclonal antibody. Thus, antibodies are preferred therapeutical monoclonal antibody-binding agents. As an example of such a therapeutical antibody-binding agent (see below example 1), polyclonal rabbit anti-Human IgG Fc may be added, which bind most relevant therapeutic monoclonal antibody molecules together at sites other than the binding site for the target of the relevant therapeutic monoclonal antibody.

Accordingly, in a highly preferred embodiment, the method of the present disclosure comprises the further addition to the reaction liquid of a therapeutic monoclonal antibody-binding agent capable of binding individual therapeutic monoclonal antibody molecules together at sites other than the binding site for the target of the relevant therapeutic monoclonal antibody, i.e. bindings that do not prevent the binding between the therapeutic monoclonal antibody and its target. Preferably, such an additional ligand is a polyclonal antibody against the therapeutic monoclonal antibody directed at regions of the therapeutic monoclonal antibody molecules that does not interact in the binding to the target of the relevant therapeutic monoclonal antibody. As such therapeutic monoclonal antibody-binding agent, any compound or protein (preferably an antibody) may be used that more or less specifically binds to two or more of the relevant therapeutic monoclonal antibodies but does not interact in the binding to the target of the relevant therapeutic monoclonal antibody. Such agent may be selected from the list consisting of anti-Ig, such as Fc-specific or Fab-specific antibodies, protein G, Protein A, Protein H, Protein L, and Protein A/G fusion protein. Accordingly, the therapeutic monoclonal antibody-binding agent may be selected to specifically bind the particular subtype of the TNF alpha inhibitor, such as when using Protein A to bind with high affinity to human IgG1 and IgG2.

It is to be understood that the therapeutic monoclonal antibody-binding agent is not usually intended to be specific to a particular therapeutic monoclonal antibody. Usually, the therapeutic monoclonal antibody-binding agent will bind different antibodies with different specificities within the same or different classes or subtypes of antibodies.

Further, importantly, the addition to the assay of a therapeutic monoclonal antibody-binding agent, i.e. agent capable of binding individual therapeutic monoclonal antibody molecules together at sites other than the binding site for the target of the relevant therapeutic monoclonal antibody, allows for the assay to detect neutralizing anti-drug antibodies and disregard non-neutralising anti-drug antibodies. This is believed to be due to the functioning of the therapeutic monoclonal antibody-binding agent itself as an artificially added non-neutralising antibody binding the therapeutic monoclonal antibody and thereby facilitating the enhancement of the assay.

Thus, in one aspect the aspects of the disclosed embodiments relates to the specific detection of neutralizing antibodies against therapeutic monoclonal antibodies. In this particular assay, the therapeutic monoclonal antibody-binding agent should preferably be added in an amount (molar) corresponding to the amount of target to the therapeutic monoclonal antibodies added to the assay, i.e. it should be added in an amount of at least 0.1 times the amount of target in the assay, such as at least 0.5 times the amount of target in the assay, such as at least 1.0 times the amount of target in the assay.

In a highly preferred embodiment of the present disclosure, the first and the second moieties are both solid particles of identical or different sizes, such as polystyrene particles, latex particles, sepharose or agarose beads or beads of other polysaccharide polymers, or magnetic or paramagnetic beads. Further, in a highly preferred embodiment, when the first and the second moieties are moieties that do not function in pairs, i.e. are both solid particles, a therapeutic monoclonal antibody-binding agent capable of ligating one therapeutic monoclonal antibody with another therapeutic monoclonal antibody, is preferably used.

In another preferred embodiment of the present disclosure, the conjugates comprise a first and a second conjugate functioning in a pair. Such pairs are for example a first conjugate comprising the target of the therapeutic monoclonal antibody conjugated to an enzyme and a second conjugate comprising the target of the therapeutic monoclonal antibody conjugated to a substrate for the enzyme. Accordingly, in a preferred embodiment of the invention, the first moiety is an enzyme and the second moiety a substrate for the first moiety. As a preferred example of such system is the horseradish peroxidase (HRP) system.

In another preferred embodiment of the present disclosure, such pairs are for example a first conjugate comprising the target of the therapeutic monoclonal antibody conjugated to a fluorophore and a second conjugate comprising the target of the therapeutic monoclonal antibody conjugated to a modulator of the fluorophore (such as a quencher). Accordingly, in a preferred embodiment of the present disclosure, the first moiety is a fluorophore and the second moiety is a modulator of the fluorescence provided by the first moiety. As preferred examples of such systems are homogeneous antibody-based proximity extension assays such as the fluorescence based Alpha screen from Perkin Elmer or the chemiluminescence based SPARCL (Spatial Proximity Analyte Reagent Capture Luminescence) technology from Beckman Coulter.

According to the aspects of the disclosed embodiments, fluorophore means an agent or means, the presence of which in the reaction and detection liquid causes the emission of detectable electromagnetic radiation (light), such as a photoluminescent or chemiluminescent marker compound. In a preferred embodiment, the fluorophore is an agent that emits detectable light in response to being contacted or irradiated with light of a different wavelength.

Spiking Assay

It was surprisingly found possible to validate the measurement of the amount of the therapeutic monoclonal antibody measured by the method according to the aspects of the disclosed embodiments (by detecting the presence/absence of patient-derived anti-drug-antibodies), and/or to detect and quantify the level of patient-derived anti-drug-antibodies in the sample in the same assay by use of an indirect measurement, where samples are spiked with a known amount of the respective therapeutic monoclonal antibody.

By comparing an obtained measurement with the expected result of such measurement (comprising a spiked amount of therapeutic monoclonal antibody) the presence/absence of anti-drug-antibodies in the sample could be established. If such neutralising anti-drug-antibodies are present, the measured amount of therapeutic monoclonal antibody is less than the expected (true) amount in the spiked sample. If non-neutralising anti-drug-antibodies are present in the sample, the measured amount of therapeutic monoclonal antibody is either identical to or higher than the expected (true) amount in the spiked sample. If non-neutralising anti-drug-antibodies are present, and the assay, including the assay of the internal standard measurement, comprises the addition of a sufficient amount of therapeutic monoclonal antibody-binding agent (in large excess of the presence of non-neutralising antibodies), the measured amount of therapeutic monoclonal antibody is identical to the expected (true) amount in the spiked sample.

By comparing more than one obtained measurement with the corresponding expected results of such measurement, the quantity of anti-drug-antibodies in the sample can be established (see example 2 below).

Thereby, surprisingly, the presence of both the relevant therapeutic monoclonal antibodies and its corresponding anti-drug antibodies can be performed in a single assay.

In its simplest aspect, the amount of the relevant therapeutic monoclonal antibody in the sample may be determined in the presence of one or more known amounts of the relevant therapeutic monoclonal antibody (which may be added to the detection liquid or to the sample prior to detection) and the amount of the relevant therapeutic monoclonal antibody including the spiked addition is determined. In case of absence of anti-drug antibodies (ADAs), the obtained result will reflect the amount present initially and the amount added by spiking. However, if the obtained result is lower than expected from the amount added by spiking, the presence of neutralising ADAs is confirmed. Even further, the quantity of both the relevant therapeutic monoclonal antibody and its ADAs may then be determined mathematically (see examples below) from comparing the obtained results with an internal standard. The amount of the spiked addition of relevant therapeutic monoclonal antibodies should then preferably be higher, or as high, as the expected amount present in the sample. Even more preferable the sample may be subjected to two or more assays comprising different amounts of spiked addition of the relevant therapeutic monoclonal antibody, in which case the true amount of both the relevant therapeutic monoclonal antibody and its ADAs may be determined mathematically (see examples below).

Thus, in a highly preferred embodiment, the method according to the present disclosure comprises the additional step of spiking the sample or the reaction liquid with one or more known amounts of the relevant therapeutic monoclonal antibody prior to the detection performed in step d., thereby providing a method for determining the validity of the measurement of the presence of the relevant therapeutic monoclonal antibody in the sample, and further providing a method for the determination of the presence and quantity of one or more different antibodies against the relevant therapeutic monoclonal antibody (ADAs) in the sample.

As another highly preferred aspect of the disclosed embodiments, the amount of the relevant therapeutic monoclonal antibody in the sample may be determined in a first assay according to the disclosed embodiments, whereafter the assay is repeated in the presence of a known spiked amount of the relevant therapeutic monoclonal antibody (the spike may simply be added to the detection liquid and the reaction may then be assayed again spectrophotometrically). In case the result obtained after spiking reflects the amount added by spiking, the absence of anti-drug antibodies (ADAs) is confirmed. However, if the obtained result is lower than expected from the amount added by spiking, the presence of neutralizing ADAs is confirmed. Even further, the quantity of both the relevant therapeutic monoclonal antibody and its ADAs may also then be determined mathematically (see examples below) from the known added amount (spike amount) and the corresponding observed signal. Quantitative determinations, however, require measurements on at least two differently spiked samples.

Thus, the aspects of the disclosed embodiments then relates to a method for determining the presence and quantity of a therapeutic monoclonal antibody, and/or a method for determining the presence and quantity of an antibody against a therapeutic monoclonal antibody, and/or a method for determining the presence and quantity of a therapeutic monoclonal antibody and the subsequent determining of the presence and quantity of corresponding therapeutic monoclonal antibody-antibody (ADA) a blood sample, the method comprising the steps of:

a. providing a first conjugate comprising the target of the therapeutic monoclonal antibody and a first conjugated moiety,
b. providing a second conjugate comprising the target of the therapeutic monoclonal antibody and a second conjugated moiety,
c. providing a reaction liquid comprising the first and the second conjugates and adding the sample to the reaction liquid, thereby forming a first detection liquid comprising the sample (potentially comprising the therapeutic monoclonal antibody) and the first and the second conjugates,
d. detecting the spectrophotometric change in signal (e.g. absorbance or luminescence) of the detection liquid following the addition of the sample in step c, (when the complex comprising the therapeutic monoclonal antibody and the first and the second conjugates is formed) by spectrophotometric measurement of the first detection liquid, and
e. determining the apparent quantity of the therapeutic monoclonal antibody in the first detection liquid,
f. adding a known amount of the therapeutic monoclonal antibody to the first detection liquid, thereby forming a second detection liquid comprising the known amount of the therapeutic monoclonal antibody, the sample (potentially comprising the therapeutic monoclonal antibody), the first and the second conjugates,
g. detecting the change in spectrophotometric signal (e.g. absorbance or luminescence) of the second detection liquid following the addition of the known amount of the therapeutic monoclonal antibody in step f (when the complex comprising the therapeutic monoclonal antibody and the first and the second conjugates is formed) by spectrophotometric measurement of the second detection liquid, and
h. determining the apparent quantity of the therapeutic monoclonal antibody in the second detection liquid, and
i. determining the presence or absence of the therapeutic monoclonal antibody and/or therapeutic monoclonal antibody antibodies.

The determination in steps e) and h) are simply made by reference to internal standard samples comprising known amounts of the therapeutic monoclonal antibody In case the apparent quantity of the therapeutic monoclonal antibody in the second detection liquid (e.g. subtracted the apparent quantity of the therapeutic monoclonal antibody in the first detection liquid) reflects the added (spiked) amount of the therapeutic monoclonal antibody, the apparent quantity of the therapeutic monoclonal antibody in the first detection liquid reflects the true amount of the therapeutic monoclonal antibody present in the sample.

In case the apparent quantity of the therapeutic monoclonal antibody in the second detection liquid (e.g. subtracted the apparent quantity of the therapeutic monoclonal antibody in the first detection liquid) is lower than would be expected from the added (spiked) amount of the therapeutic monoclonal antibody, the presence of neutralizing therapeutic monoclonal antibody antibodies is confirmed. The true amount of both the therapeutic monoclonal antibody and the corresponding neutralizing therapeutic monoclonal antibody antibodies (ADA) may be determined mathematically (as illustrated in the examples below), requiring measurements on at least two differently spiked samples.

In case the apparent quantity of the therapeutic monoclonal antibody in the second detection liquid (e.g. subtracted the apparent quantity of the therapeutic monoclonal antibody in the first detection liquid) is higher than would be expected from the added (spiked) amount of the therapeutic monoclonal antibody, the presence of non-neutralizing therapeutic monoclonal antibody antibodies is confirmed. The true amount of both the therapeutic monoclonal antibody and the corresponding non-neutralizing therapeutic monoclonal antibody antibodies (ADA) may be determined mathematically (as illustrated in the examples below).

Interestingly, the assay of the disclosed embodiments is capable of distinguishing between therapeutic monoclonal antibody antibodies (ADAs) that are "neutralising" and ADAs that are "non-neutralising". Neutralising ADAs are of particular interest as these ADAs inhibit the function of the therapeutic monoclonal drug (by inhibiting the binding between the target and the therapeutic monoclonal drug). Only the presence of neutralising antibodies in a sample will result in a decreased signal (decreased formation of complexes in the turbidity assay), whereas the presence of non-neutralising antibodies will in some cases result in a slightly increased signal (e.g. increased formation of complexes in the turbidity assay).

In general, it is preferable to exclude the impact of non-neutralising antibodies from the assay, thereby providing a fast and reliable assay for determining the true amount of free therapeutic monoclonal antibody and the presence/absence of neutralising therapeutic monoclonal antibody antibodies (ADAs). This may be achieved by adding a therapeutic monoclonal antibody-binding agent to the reaction liquid in step b) prior to the addition of sample. Obviously, in such aspect of the disclosed embodiments, the internal standard reference measurement must also be performed accordingly.

The term therapeutic monoclonal antibody antibodies (ADA) as used herein refers to a plurality of antibodies, which may be derived from a biological sample of a subject and which specifically recognises a particular therapeutic monoclonal antibody. It may be a plurality of antibodies within the same class or isotypes of antibodies, such IgG, IgE, IgA, IgD, and IgM. Accordingly, in some embodiments the ADAs being detected or measured are within a particular isotype of antibodies, such as IgG and/or IgE. Typically, the specific antibodies of the biological sample have not been purified with respect to any specific component, such as specific antibodies of the biological sample. Measurement of the amount of ADA herein refers to the determination of the concentration of host-derived antibody against the therapeutic monoclonal antibodies in the subject (such as in the sample, or tissue corresponding to the sample).

Thus, the aspects of the disclosed embodiments also relates to a method for determining the presence and quantity of one or more different therapeutic monoclonal antibodies (ADAs) in one or more blood samples, the method comprising the steps of:

a. providing a first conjugate comprising the target of the therapeutic monoclonal antibody and a first conjugated moiety,
b. providing a second conjugate comprising the target of the therapeutic monoclonal antibody and a second conjugated moiety,
c. providing a reaction liquid comprising the first and the second conjugates and adding a known amount of the therapeutic monoclonal antibody to the reaction liquid, and contacting the sample with the reaction liquid, whereby a detection liquid comprising the sample (potentially comprising the therapeutic monoclonal antibody), the spike amount of the therapeutic monoclonal antibody and the first and the second conjugates, is formed (the spike amount of therapeutic monoclonal antibody may be added to the sample or to the reaction liquid),
d. detecting the spectrophotometric change in signal following step c, (when the complex comprising the therapeutic monoclonal antibody and the first and the second conjugates, is formed) of the detection liquid, and
e. determining the quantity of the therapeutic monoclonal antibody by comparing the obtained results with an internal standard,
f. determining the presence or absence of the therapeutic monoclonal antibody by comparing the obtained measurement with the measurement expected from the added known amount of the therapeutic monoclonal antibody.

A change in signal that is less than would be expected following the addition of sample and spike to the reaction liquid indicates the presence of therapeutic monoclonal antibodies.

In a preferred embodiment, at least one repetition of the steps a-f is performed with a second spike of a known amount of a therapeutic monoclonal antibody, or alternatively comprising the additional steps g and h of providing a second spike of a known amount of the therapeutic monoclonal antibody, adding the second spike to the detection liquid following step d, and, subsequently detecting the change in signal provided by the addition of the second spike, and determining the quantity of therapeutic monoclonal antibodies in the sample.

In another aspect of the disclosed embodiments, adding a second spike comprising a therapeutic monoclonal antibody that is different from the therapeutic monoclonal antibody added in the first spike allows for the assessment of potential neutralisation of the second therapeutic monoclonal antibody. Thereby, patients may be informed if the switch of treatment between two different therapeutic monoclonal antibodies is expected to be successful (e.g. in case of the presence of ADAs in the blood of the patient).

Since the method according to the disclosed embodiments can be performed universally on different types of therapeutic monoclonal antibodies, the method according to the aspects of the disclosed embodiments is highly suited for the provision of a universal assay applicable directly in the clinic for the measurement of levels of prescribed medicaments (drugs) in individual patients.

Accordingly, in a preferred embodiment, the therapeutic monoclonal antibody is a prescription medicament. Presently preferred prescription medicaments are selected among etanercept (Enbrel), infliximab (Remicade), adalimumab (Humira), certolizumab pegol (Cimzia), and golimumab (Simponi).

However, in certain aspects of the disclosed embodiments therapeutical monoclonal antibodies targeting TNF-alpha are not preferred, and are not comprised of certain aspects of the disclosed embodiments.

In one embodiment, there is provided a kit of parts for determining the quantity of a therapeutic monoclonal antibody in a sample and/or for determining the quantity of a therapeutic monoclonal antibody-in a sample, the kit of parts comprising:

a first conjugate comprising the target of the therapeutic monoclonal antibody and a first conjugated moiety,
a second conjugate comprising the target of the therapeutic monoclonal antibody and a second conjugated moiety,
one or more standard solutions each comprising a known amount of a therapeutic monoclonal antibody drug.

Preferred devices for the detection measurements according to the aspects of the disclosed embodiments are devices capable of detecting the signal produced or ameliorated in a 200 µl or less sample detection liquid. Such devices include e.g. for example the Atolyzer® and similar devices such as devices according to e.g. EP2281631 and related applications in the name of Atonomics A/S.

Preferably, the kit of parts comprises a standard solution (spiking solution) of more than one therapeutic monoclonal antibody, such as preferably at least two different spike standard solutions comprising at least two different therapeutic monoclonal antibodies. In a preferred embodiment the kit of parts comprises at least three, such as at least four, different spike standard solutions comprising at least three, such as at least four, different therapeutic monoclonal antibody drugs.

In a highly preferred embodiment the kit of parts comprises at least one standard spike solution of the therapeutic monoclonal antibody.

In a preferred embodiment, the kit of parts also comprises a therapeutic monoclonal antibody-binding agent, i.e. a ligand capable of binding individual therapeutic monoclonal antibodies together. Preferably, such an additional ligand is a polyclonal antibody, or an antibody directed at regions of the therapeutic monoclonal antibody molecules that does not interact in the binding to the target of the therapeutic monoclonal antibody.

When measuring ADAs it is of importance is to identify the neutralizing ADAs from the non-neutralizing ADAs. Combining the patients' non-responder profile with the spike recovery method described in this patent application makes it possible to propose a treatment regime for patients with insufficient clinical response to particular drug.

The assay according to the aspects of the disclosed embodiments may also include measurement of the IgG4 antibodies in the pool of potential neutralizing ADAs. Detecting IgG4 antibodies has always been a challenges for the "bridge"-based ELISA assays since IgG4 antibodies are monovalent.

In another embodiment, the present disclosure relates to a method of treatment of a disease in a patient being treated with a therapeutic monoclonal antibody drug, said method comprising performing the method according to the aspects of the disclosed embodiments on a sample derived from the patient to determine whether the patient requires either an altered dosage regime of the therapeutic monoclonal antibody drug or an alternative therapeutic monoclonal antibody drug or an alternative pharmaceutical therapy.

The method according to the aspects of the disclosed embodiments may also be used for identifying primary non- or low-responders for a particular therapeutic monoclonal antibody treatment. These may, for example, be patients that happen to have an innate or a pre-developed immunoglobulin response to the therapeutic monoclonal antibody.

Thus, in another embodiment, the aspects of the present disclosure related to a method of identifying the optimal therapeutic monoclonal antibody drug treatment of a disease in a patient, said method comprising performing the method according to the invention on a sample derived from the patient to determine whether the patient requires either an altered dosage regime of the therapeutic monoclonal antibody drug or an alternative therapeutic monoclonal antibody drug or an alternative pharmaceutical therapy.

The method according to the aspects of the disclosed embodiments may also, for example, be used for identifying patients with secondary response failure. Secondary response failures can be asymptomatic, i.e. the only symptoms are that the treatment has become less effective or even non-effective. In this instance, the use of the method according to the aspects of the disclosed embodiments can be used to identify the development of secondary response failure before the patient or the medical practitioner has noticed that the treatment is less effective. A higher dosage of treatment may be applied to ensure that the correct and effective in vivo concentration is achieved, or alternative treatments can be selected, or a combination thereof.

Accordingly, the aspects of the disclosed embodiments comprise a method of determining whether the lack of treatment response in a patient is due to the formation of patient-derived antibodies against the therapeutic monoclonal antibody. The aspects of the disclosed embodiments thus provide for a method of selecting the appropriate drug treatment for a patient suffering from a disease which is treatable with a therapeutic monoclonal antibody (using the method steps referred to herein).

EXAMPLES

Assay Principle
TNFα (human) is immobilized onto carboxylated polystyrene particles (R1). The TNF-alpha inhibitor drug binds to the TNFα coated particles and facilitates particle agglutination. To enhance the particle agglutination reaction (in response to the presence of TF alpha inhibitor drugs), a polyclonal rabbit anti-Human IgG Fc is added (R2) which interacts with the TNF-alpha inhibitor molecules.

Reagent 1 (Reaction liquid): HEPES pH 7.2 10 mmol/L Polyethylenglycol (PEG), NaCl, human TNFα molecules bound to carboxylated polystyrene particles, detergents and stabilizers.

Reagent 2: Borate buffer 4.6 mmol/L. Polyclonal rabbit anti-Human IgG Fc, polyethylenglycol (PEG), NaCl, detergents and stabilizers.

Example 1. Therapeutical Monoclonal Antibody Assay

The objective of example 1 was to investigate if different TNFα drugs (Enbrel and Humira) could be measured using the developed assay principle (in the embodiment of particle enhanced immunoturbidimetric measurements) having an identical affinity ligand (TNFα) attached to the particles in separate assays (Enbrel array and Humira assay).
Samples
Etanercept was spiked in human plasma which did not contain any kind of drug or anti-drug antibodies and was measured using the particle-enhanced immunoturbidimetric method. The data are shown in Table 2.

Adalimumab (Humira) was spiked in human plasma which did not contain any kind of drug or anti-drug antibodies and was measured using the particle-enhanced immunoturbidimetric method. The data are shown in Table 2.
Assay Principle
Assay
The sample containing the TNF-alpha inhibitor was added to a reaction liquid containing reagent 1. Reagent 2 was added to the reaction and the development in the absorbance at 570 nm was measured.

TABLE 2

Adalimumab and Etanercept are measured using the particle-enhanced immunoturbidimetric method.

| Drug concentration (μg/mL) spiked in human plasma. | Adalimumab Absorbance (570 nm) | Etanercept Absorbance (570 nm) |
|---|---|---|
| 0 | 0.000227 | 0.000827 |
| 0 | 0.000214 | 0.000695 |
| 0 | 0.000251 | 0.000751 |
| 1.0 | 0.0489 | 0.0255 |
| 1.0 | 0.0476 | 0.0243 |
| 1.0 | 0.0463 | 0.0236 |
| 5.0 | 0.188 | 0.0961 |
| 5.0 | 0.191 | 0.0968 |
| 5.0 | 0.195 | 0.0977 |
| 10.0 | 0.394 | 0.201 |
| 10.0 | 0.397 | 0.211 |
| 10.0 | 0.386 | 0.203 |

As seen in Table 2 and each of the two TNFα-inhibiting anti-inflammatory drugs generates different signals at different concentrations in the immunoturbidimetric assay setup which is most likely due to different affinities towards the TNFα molecule immobilized on the polystyrene particles.

The data for Adalimumab Absorbance showed a linear response of $y=0.0202x+0.0011$ ($R^2=0.9976$). The data for Eternacept Absorbance showed a linear response of $y=0.0378x+0.0029$ ($R^2=0.9989$).

This example shows that accurate measurements of the concentration of different TNF-alpha inhibitors in human samples (free of anti-drug-antibodies) are possible by use of the described method.

The data of Table 2 may be seen as the internal standard for Adalimumab and Etanercept.

In the absence of ADAs in the sample, the initial performing of the assay on a sample with unknown concentrations of Adalimumab/Etanercept should readily give spectofotometric readings correlating to the true concentration in the sample by reference to the standard of Table 2.

However, detecting the presence/absence of neutralising ADAs in the sample (and thereby confirming/disconfirming the reliability of the initial measurement), spiking the samples with a known amount of Adalimumab/Etanercept, and performing the measurements also on the spiked sample are necessary. In the case of the presence of neutralising ADAs, performing the assay on a sample with spiked amounts of Adalimumab/Etanercept should give spectofotometric readings that are lower than expected from the true concentration in the sample by reference to the standard of Table 2 (lower slope of curve).

The amount of Adalimumab/Etanercept and neutralising ADAs may be determined mathematically as seen below, however, requiring at least two measurements of different spiked samples.

Example 2. Measuring the Presence of Anti-Drug-Antibodies (ADAs)

The objective of example 2 was to investigate if the method can be used to detect the presence of ADAs.

Spike and recovery can be used for validating the analytical validity of immunoassays. If there are no other species of binders competing for the analyte, and a known amount of analyte is added to a human blood, serum or plasma sample, then subsequent analysis of the spiked sample should yield 100% of the spiked amount of analyte within the error bounds of the assay, which are typically +/−5%.

For example, if 2 ug/mL of drug were spiked into a normal human sample, one would expect that between 1.90 ug/mL and 2.10 ug/mL would be found on subsequent analysis.

However, spiking a known amount of drug into a patient (or a sample therefrom) who had been injecting this drug subcutaneously for several months might give a recovery that is considerably less due to presence of ADAs.

Two or more spike and recovery points may enable the quantitative determination of the concentration of ADAs and their average affinity constant.

Interactions between binding proteins such as antibodies and their target analytes are governed by the Law of Mass Action (Eq 1)

$$K=C/(Ag)(Ab) \qquad 1.$$

Where C is the molar concentration of antibody-analyte complex, Ag is the concentration of free or unbound analyte and Ab is the concentration of antibody not bound in a complex with analyte.

This equation can be rewritten in terms of x which is the fraction of total analyte (Ag0) bound in the complex $$C=x \text{ Ago where} \qquad 2.$$

$$Ag=(1-x)Ago \qquad 3.$$

$$Ab=Abo-xAgo \qquad 4.$$

Substituting produces Equation 5

$$K=xAgo/((1-x)Ago*(Abo-xAgo)) \qquad 5.$$

Which simplifies to Equation 6

$$K=x/(1-x)(Abo-xAgo) \qquad 6.$$

Multiplying through and transposing yields Equation 7

$$(1-x)*(Abo-xAgo)=x/K \text{ which can be further simplified to Equation 8} \qquad 7.$$

$$Abo-x(Ago+Abo)+x^{2}Ago=x/K \text{ and in turn leads to Equation 9} \qquad 8.$$

$$X^{2}Ago-x(Ago+Abo+1/K)+Abo=0 \qquad 9.$$

On examination, Equation 9 is in the form of a quadratic equation and has the solution given in Equation 10

$$X=((b^{\wedge}2-4ac)^{1/2})/@=2a \qquad 10.$$

Where a=Ago, b=Ago+Abo+1/K and c=Abo

TABLE 3

For assumed values of K and Abo, the table shows the amounts of bound and free drug for various levels of total drug (Ago)

| ug/mL | [Drug] | b | X | Bound Drug | Free Drug |
|---|---|---|---|---|---|
| 0.05 | 3.33E−10 | 3.84E−07 | 8.69E−01 | 0.04 | 0.01 |
| 1 | 6.67E−09 | 3.90E−07 | 8.68E−01 | 0.87 | 0.13 |
| 2 | 1.33E−08 | 3.97E−07 | 8.66E−01 | 1.73 | 0.27 |
| 3 | 2.00E−08 | 4.03E−07 | 8.63E−01 | 2.59 | 0.41 |
| 5 | 3.33E−08 | 4.17E−07 | 8.59E−01 | 4.30 | 0.70 |
| 8 | 5.33E−08 | 4.37E−07 | 8.52E−01 | 6.82 | 1.18 |
| 12 | 8.00E−08 | 4.63E−07 | 8.42E−01 | 10.10 | 1.90 |
| 16 | 1.07E−07 | 4.90E−07 | 8.30E−01 | 13.29 | 2.71 |
| 32 | 2.13E−07 | 5.97E−07 | 7.71E−01 | 24.69 | 7.31 |
| K | 2.00E+07 | | 20 | | |
| Ab | 3.33E−07 | | 10 | 5 ug/mL | |

In the presence of antidrug antibodies, only the free drug is capable of being measured in the assay. Drug bound in an antidrug antibody complex cannot participate in another binding interaction due to steric hindrance.

In the situation where the total amount of drug is 8 ug/mL, the apparent amount of free drug would be measured as 1.18 ug/mL.

If we were to spike in an additional 4 ug/mL of drug, the total drug concentration would now be 12 ug/mL. But the observer who can only see free drug levels would detect only 1.90 ug/mL and not the 1.18 ug/mL plus the 4 ug/mL spike or 5.18 ug/mL. Only 36.6% of the expected drug level would be seen, as the vast majority of the drug both endogenous and spike is tied up in the antidrug complex.

Thereby, the method can be used to estimate the true level of ADAs in the sample.

Example 3 Drug Assay Procedure (IL17A)

The objective of example 3 was to investigate if different therapeutic monoclonal antibodies (IL17A targeted drugs) could be measured using the developed assay principle (in the embodiment of particle enhanced immunoturbidimetric measurements).

Assay Principle

IL17A (human) is immobilized onto carboxylated polystyrene particles (R1).

The IL17A inhibitor drug binds to the IL17a coated particles and facilitates particle agglutination. To enhance the particle agglutination reaction (in response to the presence of IL17A inhibitor drugs), a polyclonal rabbit anti-Human IgG Fc is added (R2) which interacts with the ID 7A inhibitor molecules.

Reagent 1: HEPES pH 7.2 10 mmol/L Polyethylenglycol (PEG), NaCl, human IL17A molecules bound to carboxylated polystyrene particles, detergents and stabilizers.

Reagent 2: Borate buffer 4.6 mmol/L. Polyclonal rabbit anti-Human IgG Fc, polyethylenglycol (PEG), NaCl, detergents and stabilizers.

The IL17A Drug Assay Procedure

The objective of example 3 was to investigate if an IL17A drug (such as brodalumab or secukinumab), could be measured using the developed assay principle (in the embodiment of particle enhanced immunoturbidimetric measurements) having an identical affinity ligand (IL17A) attached to the particles in separate assays (such as brodalumab, secukinumab or ixekizumab).

Samples

An antibody against IL17A (IL17A-Ab1) was spiked in human plasma which did not contain any kind of IL17A antibody or anti-drug antibodies and was measured using the particle-enhanced immunoturbidimetric method. The data are shown in Table 2.

An antibody against IL17A (IL17A-Ab2) was spiked in human plasma which did not contain any kind of Il17A antibody or anti-drug antibodies and was measured using the particle-enhanced immunoturbidimetric method. The data are shown in Table 2.

Assay Principle

Assay

The plasma sample containing IL17A inhibitor antibody IL17A-Ab1 or ID 7A-Ab2) was added to a reaction liquid containing reagent 1. Reagent 2 was added to the reaction and the development in the absorbance at 570 nm was measured.

TABLE 4

IL17A-Ab1 and IL17A-Ab2 are measured using the particle-enhanced immunoturbidimetric method.

| Drug concentration (µg/mL) spiked in human plasma. | IL17A-Ab1 Absorbance IL17A-Ab1 (570 nm) | IL17A-Ab2 Absorbance IL17A-Ab2 (570 nm) |
| --- | --- | --- |
| 0 | 0.000234 | 0.000843 |
| 0 | 0.000232 | 0.000691 |
| 0 | 0.000255 | 0.000764 |
| 1.0 | 0.0491 | 0.0257 |
| 1.0 | 0.0477 | 0.0248 |
| 1.0 | 0.0465 | 0.0234 |
| 5.0 | 0.195 | 0.0967 |
| 5.0 | 0.199 | 0.0975 |
| 5.0 | 0.194 | 0.0979 |
| 10.0 | 0.398 | 0.209 |
| 10.0 | 0.391 | 0.210 |
| 10.0 | 0.395 | 0.205 |

The data for IL17A-Ab1 Absorbance showed a linear response of $y=0.039x+0.0036$ ($R^2=0.9994$). The data for IL17A-Ab2 Absorbance showed a linear response of $y=0.0205x+0.0009$ ($R^2=0.9978$).

The invention claimed is:

1. A method for determining the presence and quantity of a therapeutic monoclonal antibody in a biological sample, the method comprising the steps of:
   a. providing a first conjugate comprising the target of the therapeutic monoclonal antibody and a first conjugated moiety, wherein the target of the therapeutic monoclonal antibody cannot be TNF-α,
   b. providing a second conjugate comprising the target of the therapeutic monoclonal antibody and a second conjugated moiety, wherein the first and the second moieties are both solid particles further comprising adding an agent capable of ligating one therapeutic monoclonal antibody with another therapeutic monoclonal antibody, or wherein the first moiety is an enzyme and the second moiety a substrate for the first moiety, or wherein the first moiety is an fluorophore and the second moiety a modulator of the fluorescence provided by the first moiety,
   c. providing a reaction liquid comprising the first and the second conjugates and contacting the sample with the reaction liquid, whereby a detection liquid comprising the sample potentially comprising the therapeutic monoclonal antibody and the first and the second conjugates is formed,
   d. detecting the change in spectrophotometric signal of the detection liquid following contacting the sample with the reaction liquid in step c, and
   e. determining the quantity of the therapeutic monoclonal antibody.

2. The method according to claim 1, wherein an agent capable of ligating one therapeutic monoclonal antibody with another therapeutic monoclonal antibody is added to the reaction liquid, wherein the agent is an antibody.

3. The method according to claim 1, wherein the first and the second moieties are solid particles of identical shape and size.

4. The method according to claim 1, wherein the first moiety is Horseradish Peroxidase (HRP) and the second moiety is a substrate for HRP.

5. The method according to claim 1, wherein the first moiety is a fluorophore and the second moiety a quencher.

6. The method according to claim 1, comprising the additional step of spiking the sample or the reaction liquid with one or more known amounts of the therapeutic monoclonal antibody prior to the detection performed in step d.

7. A method for determining the presence and quantity of therapeutic monoclonal antibody and/or an antibody against a therapeutic monoclonal antibody and/or a neutralizing antibody against a therapeutic monoclonal antibody in a biological sample, the method comprising the steps of:
   a. providing a first conjugate comprising the target of the therapeutic monoclonal antibody and a first conjugated moiety, wherein the target of the therapeutic monoclonal antibody cannot be TNF-α,
   b. providing a second conjugate comprising the target of the therapeutic monoclonal antibody and a second conjugated moiety, wherein the first and the second moieties are solid particles further comprising adding an agent capable of ligating one therapeutic monoclonal antibody with another therapeutic monoclonal antibody, or wherein the first moiety is an enzyme and the second moiety a substrate for the first moiety, or wherein the first moiety is an fluorophore and the second moiety a modulator of the fluorescence provided by the first moiety,
   c. providing a reaction liquid comprising the first and the second conjugates and adding a known spike amount of the therapeutic monoclonal antibody to the reaction liquid, and contacting the sample with the reaction liquid, whereby a detection liquid comprising the sample, the spike amount of the therapeutic monoclonal antibody and the first and the second conjugates, is formed,
d. detecting the change in spectrophotometric signal of the detection liquid following contacting the sample with the reaction liquid in step c, and
e. determining the quantity of the therapeutic monoclonal antibody by comparing the obtained results with an internal standard,
f. determining the presence or absence of an antibody against the therapeutic monoclonal antibody and/or a neutralizing antibody against the therapeutic monoclonal antibody by comparing the obtained measurement with the measurement expected from the added known amount of the therapeutic monoclonal antibody.

8. The method according to claim 7, comprising the performance of at least one repeat of steps d-f with a second spike of a known amount of the therapeutic monoclonal antibody, or alternatively providing a second spike of a known amount of the therapeutic monoclonal antibody, or adding the second spike to the detection liquid following step d, and subsequently detecting the change in spectrophotometric signal provided by the addition of the second spike, and determining the quantity of the therapeutic monoclonal antibody in the sample.

9. The method according to claim 1, wherein the therapeutic monoclonal antibody is a prescription medicament.

10. A kit of parts for determining the quantity of a therapeutic monoclonal antibody and an antibody against a therapeutic monoclonal antibody in a sample, the kit of parts comprising:
a. a first conjugate comprising the target of the therapeutic monoclonal antibody and a first conjugated moiety, wherein the first conjugated moiety is a solid particle, an enzyme, or a fluorophore,
b. a second conjugate comprising the target of the therapeutic monoclonal antibody and a second conjugated moiety, wherein the second conjugated moiety is a solid particle, a substrate for the first moiety, or a modulator of the fluorescence provided by the first moiety, wherein where either the first or the second conjugated moiety is a solid particle, further comprising an agent capable of ligating one therapeutic monoclonal antibody with another therapeutic monoclonal antibody,
c. one or more spike standard solutions each comprising a known amount of the therapeutic monoclonal antibody.

11. The kit of parts according to claim 10, further comprising a therapeutic monoclonal antibody-binding agent capable of ligating one therapeutic monoclonal antibody with another therapeutic monoclonal antibody, wherein the agent is an antibody.

12. The kit of parts according to claim 10, comprising at least two different spike standard solutions comprising different therapeutic monoclonal antibodies.

13. The method according to claim 7, wherein the first and the second moieties are solid particles of identical shape and size.

14. The method according to claim 7, wherein the first moiety is Horseradish Peroxidase (HRP) and the second moiety is a substrate for HRP.

15. The method according to claim 7, wherein the first moiety is a fluorophore and the second moiety a quencher.

16. A method for determining the presence and quantity of a therapeutic monoclonal antibody, and/or a method for determining the presence and quantity of an antibody against a therapeutic monoclonal antibody, and/or a method for determining the presence and quantity of a therapeutic monoclonal antibody and the subsequent determining of the presence and quantity of corresponding therapeutic monoclonal antibody-antibody (ADA) in a blood sample, the method comprising the steps of:
a. providing a first conjugate comprising the target of the therapeutic monoclonal antibody and a first conjugated moiety,
b. providing a second conjugate comprising the target of the therapeutic monoclonal antibody and a second conjugated moiety,
c. providing a reaction liquid comprising the first and the second conjugates and adding the blood sample to the reaction liquid, thereby forming a first detection liquid comprising the blood sample and the first and the second conjugates,
d. detecting the spectrophotometric change in signal of the detection liquid following the addition of the blood sample in step c, by spectrophotometric measurement of the first detection liquid, and
e. determining the apparent quantity of the therapeutic monoclonal antibody in the first detection liquid,
f. adding a known amount of the therapeutic monoclonal antibody to the first detection liquid, thereby forming a second detection liquid comprising the known amount of the therapeutic monoclonal antibody, the blood sample, and the first and the second conjugates,
g. detecting the change in spectrophotometric signal of the second detection liquid following the addition of the known amount of the therapeutic monoclonal antibody in step f by spectrophotometric measurement of the second detection liquid, and
h. determining the apparent quantity of the therapeutic monoclonal antibody in the second detection liquid, and
i. determining the presence or absence of the therapeutic monoclonal antibody and/or therapeutic monoclonal antibody antibodies, wherein the target of the therapeutic monoclonal antibody is not TNF-α.

17. The method according to claim 16, wherein the first and the second moieties are solid particles of identical shape and size.

18. The method according to claim 16, wherein the first moiety is Horseradish Peroxidase (HRP) and the second moiety is a substrate for HRP.

19. The method according to claim 16, wherein the first moiety is a fluorophore and the second moiety a quencher.

* * * * *